(12) United States Patent
Ulloa

(10) Patent No.: US 12,380,407 B2
(45) Date of Patent: *Aug. 5, 2025

(54) SYSTEM AND METHOD FOR FACILITATING DATA ACCESS AND VERIFICATION FOR ITINERATE MEDICAL PERSONNEL

(71) Applicant: Jeannette Ulloa, Irving, TX (US)

(72) Inventor: Jeannette Ulloa, Irving, TX (US)

(73) Assignee: CRE-Dense Upload, Inc., Irving, TX (US)

( * ) Notice: Subject to any disclaimer, the term of this patent is extended or adjusted under 35 U.S.C. 154(b) by 188 days.

This patent is subject to a terminal disclaimer.

(21) Appl. No.: 17/880,513

(22) Filed: Aug. 3, 2022

(65) Prior Publication Data

US 2022/0374837 A1    Nov. 24, 2022

Related U.S. Application Data

(63) Continuation-in-part of application No. 16/752,145, filed on Jan. 24, 2020, now Pat. No. 11,545,258.

(51) Int. Cl.
*G16H 50/20* (2018.01)
*G06Q 10/0631* (2023.01)
*G06Q 10/105* (2023.01)
*G16H 40/20* (2018.01)

(52) U.S. Cl.
CPC ....... *G06Q 10/105* (2013.01); *G06Q 10/0631* (2013.01); *G16H 40/20* (2018.01)

(58) Field of Classification Search
CPC ... G06Q 10/105; G06Q 10/0631; G16H 40/20
See application file for complete search history.

(56) References Cited

U.S. PATENT DOCUMENTS

| | | |
|---|---|---|
| 2004/0204948 A1 | 10/2004 | Singletary et al. |
| 2009/0177511 A1 | 7/2009 | Shaw et al. |
| 2011/0055099 A1 | 3/2011 | Paul et al. |
| 2015/0310188 A1 | 10/2015 | Ford et al. |

(Continued)

FOREIGN PATENT DOCUMENTS

WO    2006020570 A2    2/2006

OTHER PUBLICATIONS

Praos Health Inc., "Mobilizing your Nursing Workforce", https://praoshealth.com, Downloaded on Jan. 24, 2020, 6 pages.

*Primary Examiner* — Maroun P Kanaan
(74) *Attorney, Agent, or Firm* — Stephen P. McNamara; St. Onge Steward Johnston & Reens LLC

(57) ABSTRACT

A system and method for securely allowing access to personal medical worker information for itinerate medical workers working on a contract basis for various medical facilities. The system includes a documentation computer designed to interface with a healthcare provider computer when a medical worker selects a work contract associated with the healthcare provider. The medical worker's personal information is selectively shared based on user defined rules to limits potential compromising of the medical workers personal data due to a data breach or the like. Additionally, the medical worker's personal information is automatically normalized so that a healthcare provider computer can use a number of different terms in describing the data needed to be provided to fulfill the contract.

14 Claims, 27 Drawing Sheets

(56) References Cited

U.S. PATENT DOCUMENTS

2018/0301218 A1   10/2018  Bochaton
2020/0117690 A1*  4/2020  Tran .................. G06F 16/90332
2021/0090694 A1*  3/2021  Colley .................. G16H 15/00

* cited by examiner

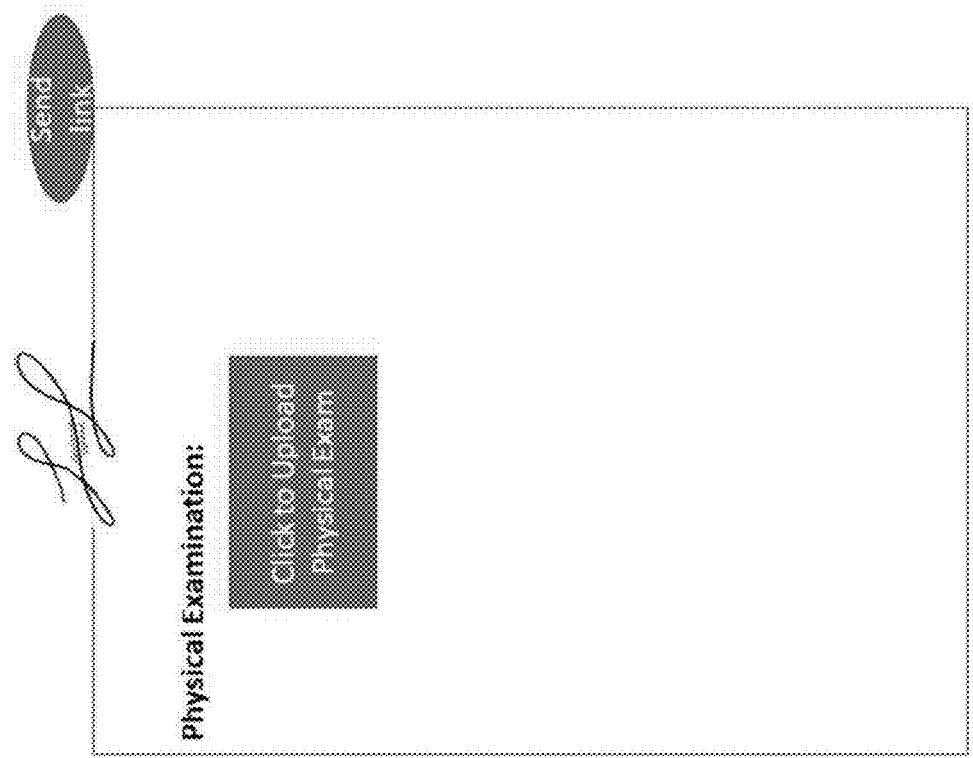
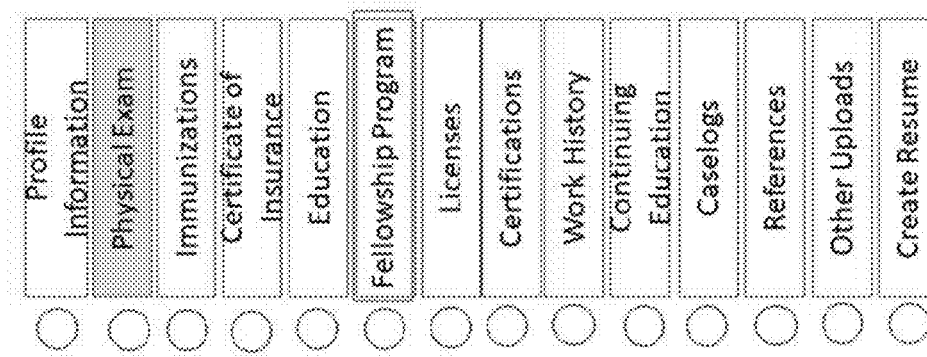
FIG. 6

Certifications:
- Professional Certification:
  - Primary specialty
  - Issuing Agency:
  - Issued Date:
  - Expiration Date:
- ACLS:
  Expiration Date:
- PALS:
  Expiration Date:
- BLS:
  Expiration Date:
- NRP:
  Expiration Date:
- Trauma:
  Expiration Date:
- Other Certifications:
  Expiration Date:

Profile Information | Physical exam | Immunizations | Certificate of Insurance | Education | Fellowship Program | Licenses | Certifications | Work History | Continuing Education | Caselogs | References | Other Uploads | Create Resume

*FIG. 12*

Work experience

Previous Practice/Employer name:

Start/End Dates:

Address:

Contact information:
* Name
* Phone number
* Email address

FIG. 13

Profile Information | Physical exam | Immunizations | Certificate of Insurance | Education | Fellowship Program | Licenses | Certifications | Work History | Continuing Education | Caselogs | References | Other Uploads | Create Resume

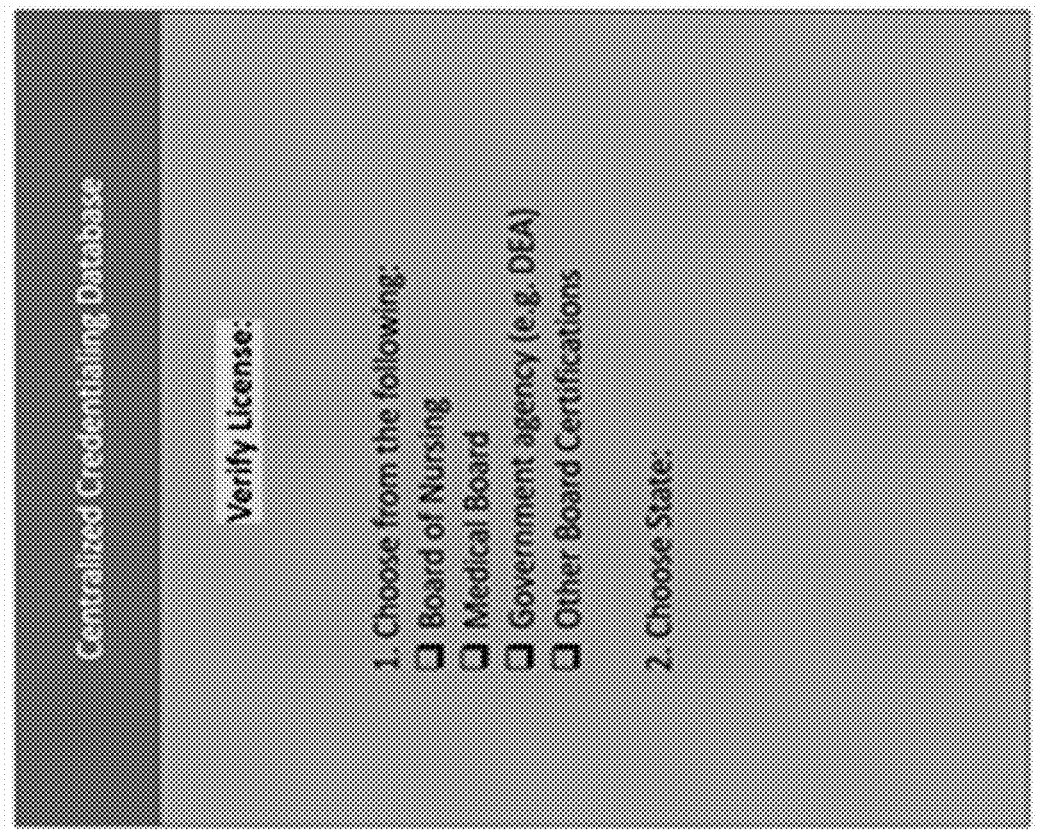
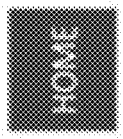
FIG. 22

SYSTEM AND METHOD FOR FACILITATING DATA ACCESS AND VERIFICATION FOR ITINERATE MEDICAL PERSONNEL

FIELD OF THE INVENTION

A system and method for facilitating the inter-facility movement of medical personnel, and more particularly, the invention is directed to a system and method for assisting itinerate medical personnel in providing the needed documentation to medical facilities prior to beginning contract work for the healthcare provider and allows the healthcare provider to verify the documentation.

BACKGROUND OF THE INVENTION

In the medical industry in the United States, itinerate medical personnel regularly pick up contracts to work for different medical facilities across the country for a set period of time. For example, a registered nurse, a physician's assistant or a medical doctor may contract to work for a hospital for a period of two months. Alternatively, the length of the contract could be a short as one or two weeks or for a longer period of time. However, each facility requires specific documentation.

The strict licensing requirements and documentation required to be provided to the healthcare provider that is contracting with the medical personnel for the contract period is no lower than that required for a permanent hire. In other words, the documentation required is intensive and may include: 1) proof of education (e.g., graduate of accredited medical school, graduate of accredited nursing program, etc.); 2) proof of licensing and all certifications (e.g., medical license in the state, nursing license/credentials in the state, pediatrics certifications, etc.); 3) proof of insurance (e.g., malpractice insurance, etc.); 4) documentation relating to any malpractice claims made against the individual; and 5) proof of immunizations/physicals/health status and so on. As such, the documentation requirements can be extremely burdensome especially when the number of different contracts picked up by the person is relatively large.

All this documentation must be transmitted ahead of time to each and every hospital or healthcare provider the individual will work in. In particular, the documentation must arrive with enough time to allow for facilities personnel to verify the information and allow time for correction of any missing or incomplete information. When an individual picks up 10-12 contracts over the course of a year, each of which may be located at diverse locations across the United States where each healthcare provider and each state may have their own documentation requirements, the documentation burden can become unwieldy.

Another issue is that there is no uniformity between medical facilities with respect to the form of the documentation and the specific required information. In other words, each healthcare provider may require documentation to be submitted in a specific format and the information may need to be modified to fit that. Additionally, the particular information required by a particular facility may vary from facility to facility.

Still another issue is that with the increase in the number of data breaches on the rise, the sharing of personal information increases the risk that personal data may be compromised. The documentation needed by various medical facilities contains personal information, such as licensure, certificate of liability and other credentialing documents. Transmission of this information via plain text email creates a risk of the information being compromised.

The risk of personal information being compromised becomes even clearer when the credentialing process is analyzed. Information is first sent to a third-party company that validates the credentials before being forwarded to the hospital. Often a hospital will require additional information to be sent directly to the hospitals' credentialing team. The exchange creates multiple opportunities for the information to be compromised, as it is passed between the individual, the third-party company, and the hospital.

In recent years, medical identity theft occurring among healthcare providers has increased dramatically. During the Covid-19 pandemic, a significant increase has been seen in number of scams and fraudulent work postings. Imposters, posing as healthcare providers, have fraudulently obtained the medical identity of some medical workers. Using fraudulently obtained medical license information, they have used these for both fraudulent medical practice and fraudulent health insurance reimbursement. These have also been used to fraudulently write prescriptions, and to scam healthcare providers.

This risk is increased for itinerate medical workers who contract with multiple facilities during the year and therefore must share sensitive personal information with multiple facilities in connection with each work contract. Still further, as the medical worker moves on to their next contracted work assignment, the healthcare provider may retain access to the medical worker's personal data even when they have completed their contract. As such, itinerate medical workers have an interest in sharing only a selected amount of personal data as needed by the healthcare provider and in only allowing access to their personal data for a specified time period.

SUMMARY OF THE INVENTION

In view of the above, a goal of the system is to provide a secure platform that is easy for a user to add documentation to while storing the documentation securely. Since the documentation is stored within the system securely, the user can modify and adjust the documentation for future credentialing needs. The application allows the user to create secure links for the parties involved to review and validate the credentials.

What is desired is a system and method for that allows for a medical worker to remotely and automatically share itinerate medical personnel information with a healthcare provider.

It is further desired to provide a system and method that allows for itinerate medical personnel to automatically share only specifically selected personal data with a healthcare provider and to automatically limit the duration for which the healthcare provider has access to that information.

It is still further desired to provide a system and method that provides for the automatic uploading of personal information relating to itinerate medical personnel that automatically is adjusted to meet the data and formatting requirements of a healthcare provider with which the medical worker has contracted.

It is also desired to provide a system and method where a healthcare provider can automatically be assured that the information provided by the medical worker is verified by a trusted source.

It is further desired to provide a system and method where a medical worker can automatically be assured that job posting by a healthcare provider is verified by a trusted source.

Finally, it is desired to provide a system and method for automatically generating medical credentials for an individual when personal medical data associated with the individual is received and processed by a healthcare provider and meets the healthcare provider's requirements.

The current system is directed to system to facilitate the automatic access to documentation for a medical worker by a healthcare provider governed by rules set up by the medical worker and a set of rules established by the healthcare provider. In one configuration, a medical documentation computer is provided having a network connection and a storage accessible by the computer. A medical worker has access to the medical documentation computer via a user computer that is connected to the network. The user can upload their personal information to be saved on the storage for access by healthcare providers. A medical contract company may act as a broker between various healthcare providers and the medical worker to present various medical contracts associated with the various healthcare providers. The medical contract company utilizes a medical contract computer connected to the network and provided with a storage having medical contract data stored thereon representative of various proposed medical worker contracts. The medical worker can access the various proposed medical worker contracts to be bid on or selected. Once the medical worker selects a particular contract, the medical contract computer can send an indication to the healthcare provider computer that an individual has selected a contract.

In one configuration, a medical worker accesses the medical documentation computer and creates an account. This may include a number of steps including providing various medical documents and licenses, as well as personal information. Once all this information is uploaded to the system, in one configuration the software that is running on the medical documentation computer can automatically verify that the provided information is accurate with the private, state and national agencies that have purportedly issued the documentation. This can be an automatic process where, for instance, the medical workers personal information (D.O.B., address, SSN and so on) can be verified with a state agency. Additionally, education information can be automatically verified with educational institutions that have purportedly issued the degree(s); or with State agencies that have purportedly issued the license(s); or with Federal agencies that have purportedly issued the certification(s). Once this process is completed, the medical worker will have a verified account. Alternatively, these steps could be delayed for a healthcare provider to prompt the software running on the medical documentation computer to verify the information that has been provided by the medical worker.

Once a medical worker identifies a contract they would like to apply for, the medical worker may then log onto the medical documentation computer and verify that the healthcare provider is reputable organization and not a scam soliciting medical worker data. The verification process could be automatically performed by software executing on the medical documentation computer and/or prompted by the medical worker. For example, in one configuration when the healthcare provider initially logs onto the medical documentation computer and sets up an account, the relevant information relating to the healthcare provider including all licenses and ID numbers used by the state in which the healthcare provider is located is provided as part of the setup and configuration process for the healthcare provider account. This information may then be verified by the software executing on the medical documentation computer, which would automatically access the state records to verify that the information provided is accurate and up to date. Alternatively, the medical worker could prompt the software to verify the identity of the healthcare provider to ensure the provider is not a scammer.

Once the medical worker confirms that the healthcare is trusted institution, they can then select what personal information is to be shared with the healthcare provider associated with the contract that was selected. Alternatively, the act of selecting the contract can function as an "approval" on the part of the user to allow the healthcare provider associated with the contract to access the information required by the medical documentation computer. The healthcare provider can be assured that the medical documentation that is being provided is true and accurate because they have the ability to verify the incoming data, or it will have already been verified by the software running on the medical documentation computer. Likewise, the medical worker can be confident that the medical documentation is not being fraudulently accessed.

It is understood that the healthcare provider associated with the contract can have specific information requirements that may be unique to or differ from other healthcare provider's data requirements. Still further, the healthcare provider may require the data to be provided in a certain type of format. As such, in one configuration it is contemplated that a healthcare provider may log into the medical documentation computer and provide a set of rules reflective of a specific format for the medical personnel data they want to receive. This rule set that is provided on the medical documentation computer, could be programmable and selectable for each healthcare provider so that specific information provided and a format in which the specific information is provided is fully customizable. In this configuration, the user, upon selection of a contract, can log onto the medical documentation computer and see precisely what information the healthcare provider will require and can enable access to that information. Alternatively, the user could automatically allow access to the information required by the healthcare provider associated with the selected contract.

Additionally, in one configuration a window of time may be provided within which the healthcare provider will have access to the information associated with the medical worker. For example, the access could range from between 24-72 hours, after which the access to the information through the medical documentation computer is no longer available. It is further contemplated that any healthcare provider that seeks access to medical documentation associated with a user will have to comply with the Health Insurance Portability and Accountability Act (HIPAA) requirements. For example, healthcare providers accessing the medical documentation of medical workers would need to utilize certificate-based encryption for access and/or transfer of data. In one configuration, no personal data of the medical worker would be allowed to be copied from the medical documentation computer, but rather, only access (for a specified duration) would be allowed. In other configurations, certain data may be allowed to be transferred but under very tight security.

Once all the needed documentation is accessed and evaluated by the healthcare provider and it is determined that all documentation is in order, only then would the healthcare provider system facilitate the producing of medical credentials for the medical worker to work at the healthcare provider associated with the particular contract. Generation of the credential could include, in one configuration, automatically creating or printing a badge that is wearable by the medical worker for the duration of the contract. The badge could include a picture of the individual, the pertinent information the healthcare provider would require on the badge and a scannable code that would include the time period for which the badge was valid.

The system provides several distinct advantages over known ways of providing personal medical information for workers to medical facilities. For example, when the user is ready to send a completed application to a third party or hospital for validation, the software generates a time limited link that generates a custom packet for the party to review in order to complete validation. This may be done manually or automatically through the rules set up by the user. The system may utilize secure socket layer technology in conjunction with encryption to ensure that the data is only accessible by the party that is responsible for the validation. Encryption used is based on the Advanced Encryption Standard (AES) algorithm.

The system also provides secure pdf/image storing techniques that ensures the data can't be accessed outside of the application. All of the documentation is stored in a folder that requires secure access. To further increase security of the files, they are validated against base64 to ensure they have not been compromised. Files are also assigned names that carry no relevant information as to what the file contains. Information on the file is stored security in the database for the software to be able to access, decrypt and process the file.

For this application the following terms and definitions shall apply:

The term "data" as used herein means any indicia, signals, marks, symbols, domains, symbol sets, representations, and any other physical form or forms representing information, whether permanent or temporary, whether visible, audible, acoustic, electric, magnetic, electromagnetic or otherwise manifested. The term "data" as used to represent predetermined information in one physical form shall be deemed to encompass any and all representations of the same predetermined information in a different physical form or forms.

The term "network" as used herein includes both networks and internetworks of all kinds, including the Internet, and is not limited to any particular network or inter-network.

The term "communications medium" as used herein means any form of electronic communication which could include a mobile device or some device that is remote from another device(s). This may include a phone, text, pager, email system, computer, tablet, app, smart phone, personal smart device and/or wearable technology, laptop and so on.

The terms "first" and "second" are used to distinguish one element, set, data, object or thing from another, and are not used to designate relative position or arrangement in time.

The terms "coupled", "coupled to", "coupled with", "connected", "connected to", and "connected with" as used herein each mean a relationship between or among two or more devices, apparatus, files, programs, applications, media, components, networks, systems, subsystems, and/or means, constituting any one or more of (a) a connection, whether direct or through one or more other devices, apparatus, files, programs, applications, media, components, networks, systems, subsystems, or means, (b) a communications relationship, whether direct or through one or more other devices, apparatus, files, programs, applications, media, components, networks, systems, subsystems, or means, and/or (c) a functional relationship in which the operation of any one or more devices, apparatus, files, programs, applications, media, components, networks, systems, subsystems, or means depends, in whole or in part, on the operation of any one or more others thereof.

The terms "process" and "processing" as used herein each mean an action or a series of actions including, for example, but not limited to, the continuous or non-continuous, synchronous or asynchronous, routing of data, modification of data, formatting and/or conversion of data, tagging or annotation of data, measurement, comparison and/or review of data, and may or may not comprise a program.

The term "object" as used herein means a distinct software module or collection of computer code that possesses (1) data that uniquely separates the module or collection of computer code from other similar modules or collections, (2) attributes constituting a predetermined subset of data types describing media data usage and/or media data users and/or any other supporting datatypes or users, and (3) behavior which (i) limits access to such attributes by responding only to requests conforming to a predetermined published interface, and (ii) gathers data of such predetermined subset or merges objects which possess such data.

As used herein, the phrases "at least one," "one or more," "or," and "and/or" are open-ended expressions that are both conjunctive and disjunctive in operation. For example, each of the expressions "at least one of A, B and C," "at least one of A, B, or C," "one or more of A, B, and C," "one or more of A, B, or C," "A, B, and/or C," and "A, B, or C" means A alone, B alone, C alone, A and B together, A and C together, B and C together, or A, B and C together.

The term "medical personnel" as used herein means any person that provides medical care and may include, but is not limited to, Physicians, Physician Assistants, Nurse Practitioners, Certified Registered Nurse Anesthetists, Advanced Practicing Registered Nurses, Registered Nurses, License Practical Nurses, and Certified Nursing Assistants.

The term "healthcare provider" as used herein means a health facility organization licensed to provide health care diagnosis and treatment services including medication, surgery and medical devices and includes pharmacies, hospitals, labs, and clinics, and may encompass any facility for the delivery of health services including but not limited to a hospital, a state mental hospital, a public health center, an outpatient medical facility, a rehabilitation facility, a facility for long-term care, a community mental health center, a migrant health center, a facility operated by a city or county health department, and a community health center.

In one configuration a system for selectively controlling access to medical personnel data is provided comprising a medical personnel records computer having a storage and coupled to a network where the medical personnel records computer is adapted to receive medical personnel data associated with a user and saved on the storage. The system is provided such that the user sets user defined rules governing access to the medical personnel data associated with the user. The system is further provided such that the user accesses a medical contract computer having a plurality of proposed medical contracts each associated with a healthcare provider and the user selects at least one of the plurality of proposed medical contracts. The medical contract computer is coupled to a healthcare provider computer associated with the medical contract selected by the user, and the medical contract computer transmits data relating to the user selected contract. The system is also provided such that the healthcare provider computer couples to the medical personnel records computer in response to receipt of the data relating to the user selected contract, and the healthcare provider computer having healthcare provider defined rules. Finally, the systems provides that the medical personnel records computer selectively allows access to the medical personnel data associated with the user according to the user defined rules, and the medical personnel records presents medical personnel data associated with the user to the healthcare provider computer based on the user defined rules and the healthcare provider defined rules.

In another configuration a method for selectively controlling access to medical personnel data is provided comprising the steps of accessing a medical personnel records computer and uploading medical personnel data associated with a user to be saved on a storage accessible by the medical personnel records computer, setting user defined rules governing access to the medical personnel data associated with a user and accessing a medical contract computer having a plurality of proposed medical contracts each associated with a healthcare provider. The method further comprises the steps of selecting at least one of the plurality of proposed medical contracts, transmitting the selection from the medical contract computer to a healthcare provider computer associated with the medical contract selected by the user and requesting medical personnel data associated with a user be accessed by the healthcare provider computer. Finally, the method comprises the steps of granting the access request of the healthcare provider computer to access the medical personnel data associated with a user when the user defined rules allow for such access and generating medical credentials when the accessed medical personnel data associated with a user is compliant with a healthcare provide defined set of rules.

Other objects of the invention and its particular features and advantages will become more apparent from consideration of the following drawings and accompanying detailed description.

BRIEF DESCRIPTION OF THE DRAWINGS

FIGS. 5-13 are various screen shots of the system allowing for the uploading of information by the user to create medical personnel data associated with a user according to the system of FIG. 1.

FIGS. 14-25 are various screen shots of the system illustrating the registering of an account with the Centralized Credentialing Database and the various functionality provided by the system.

DETAILED DESCRIPTION OF THE INVENTION

Figure 1:
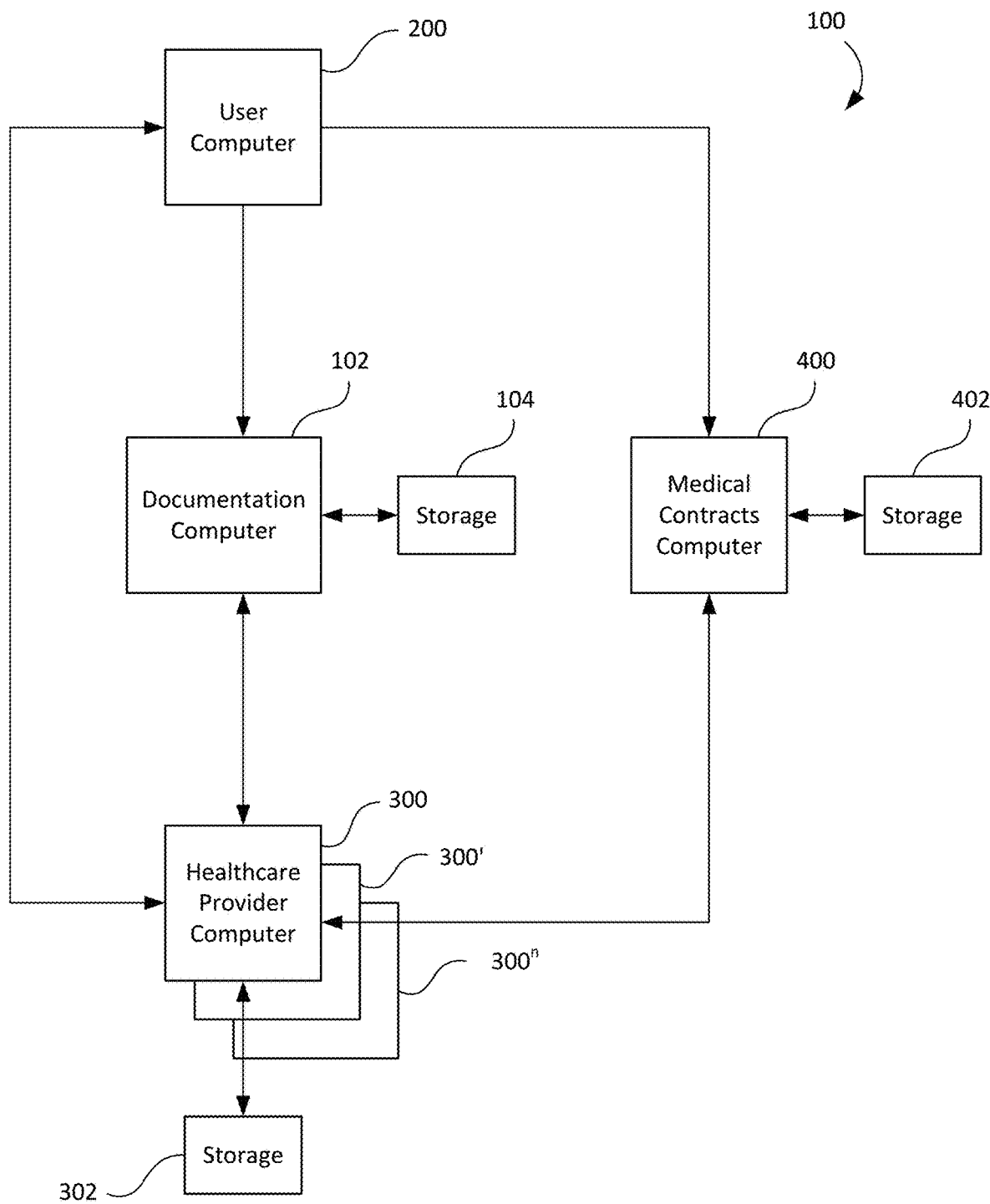
FIG. 1 is a block diagram of a system according to one configuration of the invention.

Referring now to the drawings, wherein like reference numerals designate corresponding structure throughout the views.

FIG. 1 depicts the system 100 for selectively controlling access to medical personnel data. The system 100 includes a documentation computer 102 that includes a storage 104 on which for instance, medical personnel data associated with a user is stored.

A user computer 200 may be utilized by a user to access a documentation computer 102 via a communications medium. The documentation computer 102 is adapted to receive, for example, medical personnel data associated with a user, which can be saved on storage 104. Additionally, a user can set up rules governing the sharing of the medical personnel data associated with a user, which are also saved on storage 104.

Also shown in FIG. 1 is a healthcare provider computer 300 having an associated storage 302 and a medical contracts computer 400, also having an associated storage 402. A plurality of healthcare provider computers 300, 300', 300" are depicted to illustrate than many medical facilities will be accessing and posting contracts on medical contracts computer 400. Each healthcare provider will have their own specific information that they will want to receive in connection with their posted contracts and may want to access the information in a specific file format(s).

A healthcare provider looking to hire itinerate medical workers may log onto the medical contracts computer 400 and save proposed medical contracts thereon. The healthcare provider computer 300 can also log onto the documentation computer 102 and set up a set of rules governing the type and format of medical personnel data that should be received associated with each of the various proposed medical contracts that have been posted. In one embodiment, the type of medical personnel data can include, for example, education information, licensing information, certification information, insurance information, malpractice information, immunization information, health status information and so on. Additionally, the formatting rules are provided to govern a file format in which the medical personnel data is provided to the healthcare provider.

Figure 2:
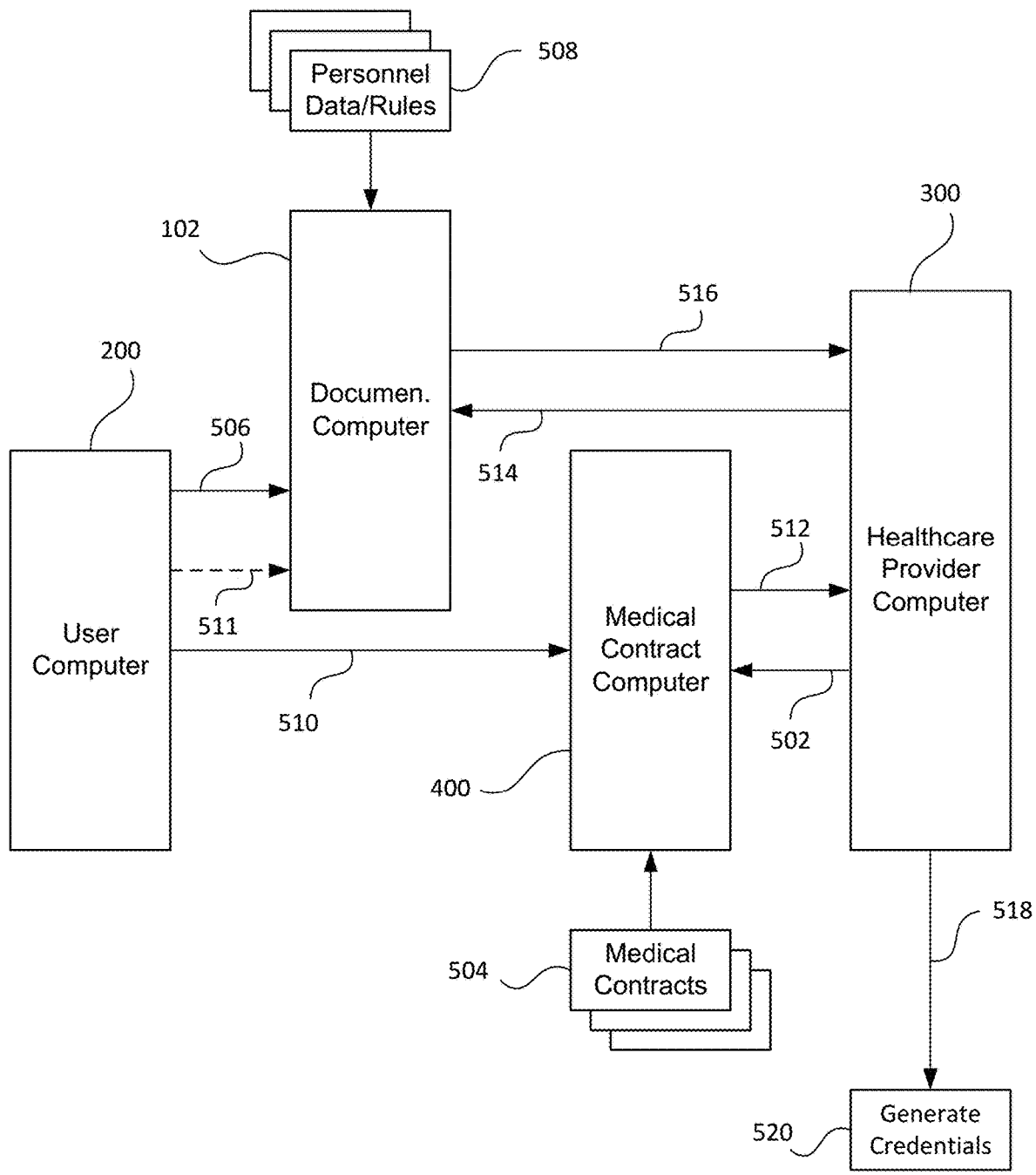
FIG. 2 is a block diagram illustrating the functioning of the system according to FIG. 1.

FIG. 2 illustrates the functional interchange of information that is shared between the user computer 200, the documentation computer 102, the healthcare provider computer 300 and the medical contracts computer 400. As previously stated, the healthcare provider computer 300 is a computer associated with a healthcare provider that is providing proposed contracts for medical workers to come and work at the healthcare provider for a specified period of time. The medical contracts computer 400 is associated with a third party that acts as a broker for medical contracts between the healthcare provider and medical workers.

As an initial step, a healthcare provider will upload or transmit 502 a proposed medical contract to medical contracts computer 400. This proposed contract or a plurality of contracts 504 will then be viewable to any user logging onto medical contracts computer 400.

Also, as an initial step, a medical worker (user) will upload or transmit 506 medical personnel data associated with the user from user computer 200 to documentation computer 102. The user will also provide a set of rules that govern access to the medical personnel data associated with the user 508.

At this point, the user may log in and access 510 the medical contracts computer 400 to view the plurality of contracts 504. If the user identifies a medical contract that the user would like to select, the user has the option to first verify the healthcare provider. This process will be described further in connection with FIG. 3B.

Once the user has verified the healthcare provider, the user can then log back onto the medical contracts computer 400 and select the contract they are interested in applying for. In one configuration, the user can then access documentation computer 102 and specifically authorize 511 a particular healthcare provider to access the medical personnel data associated with the user. Alternatively, the act of selecting the contract could act as the authorization allowing the healthcare provider associated with the selected contract to access the medical personnel data associated with the user. The selection generates a notification 512 that is transmitted from the medical contract computer 400 to healthcare provider computer 300. This automatic notification will indicate the contract selection and include information identifying the user. From this information the healthcare provider computer 300 can then send a request to documentation computer 102 to access information 514 associated with the medical worker that has selected the proposed contract.

Once the request for information is received, the documentation computer 102 will look at the rules set up by the user. This could be in one configuration, whether the user specifically authorized 511 the access, or whether the user has set up automatic authorization to follow the selection of a contract. In any event, the documentation computer 102 will allow access based on the rules defined by the user.

If the healthcare provider has authorization to view the medical personnel data associated with the user, documentation computer 102 will provide access to the requested data 516. In addition, documentation computer 102 can look at the set of rules provided by the healthcare provider and automatically provide the data (if the user rules are first satisfied) in the format the healthcare provider desires. The healthcare provider has the option to verify the user and the data provided by the documentation computer 102. This process will be described further in connection with FIG. 3A.

If the healthcare provider has been provided with all the information required, the user is verified and the healthcare provider clears the medical worker to fulfill the selected contract, the healthcare provider computer 300 can then automatically generate 518 a medical credential 520 for the user that will be valid for the duration of the contract period. The step of generating the credential 540 could include automatically creating a badge that is printed out to be worn by the medical worker for the duration of the contract.

As noted at the outset of the application, the verification of a user and their credentials has become important with the rise in identity theft as individuals seek to steal medical credentials. Unsavory individuals have used stolen medical credentials to impersonate doctors as telemedicine has proliferated during the pandemic. These stolen credentials have been used to write false prescriptions or to even impersonate medical personnel in the home healthcare field and even in hospital settings. Accordingly, it has become very important to verify the identity of medical workers and protect their identities from being stolen and confirm that the individual is who they say they are prior to beginning work for a healthcare provider.

Figure 3A:
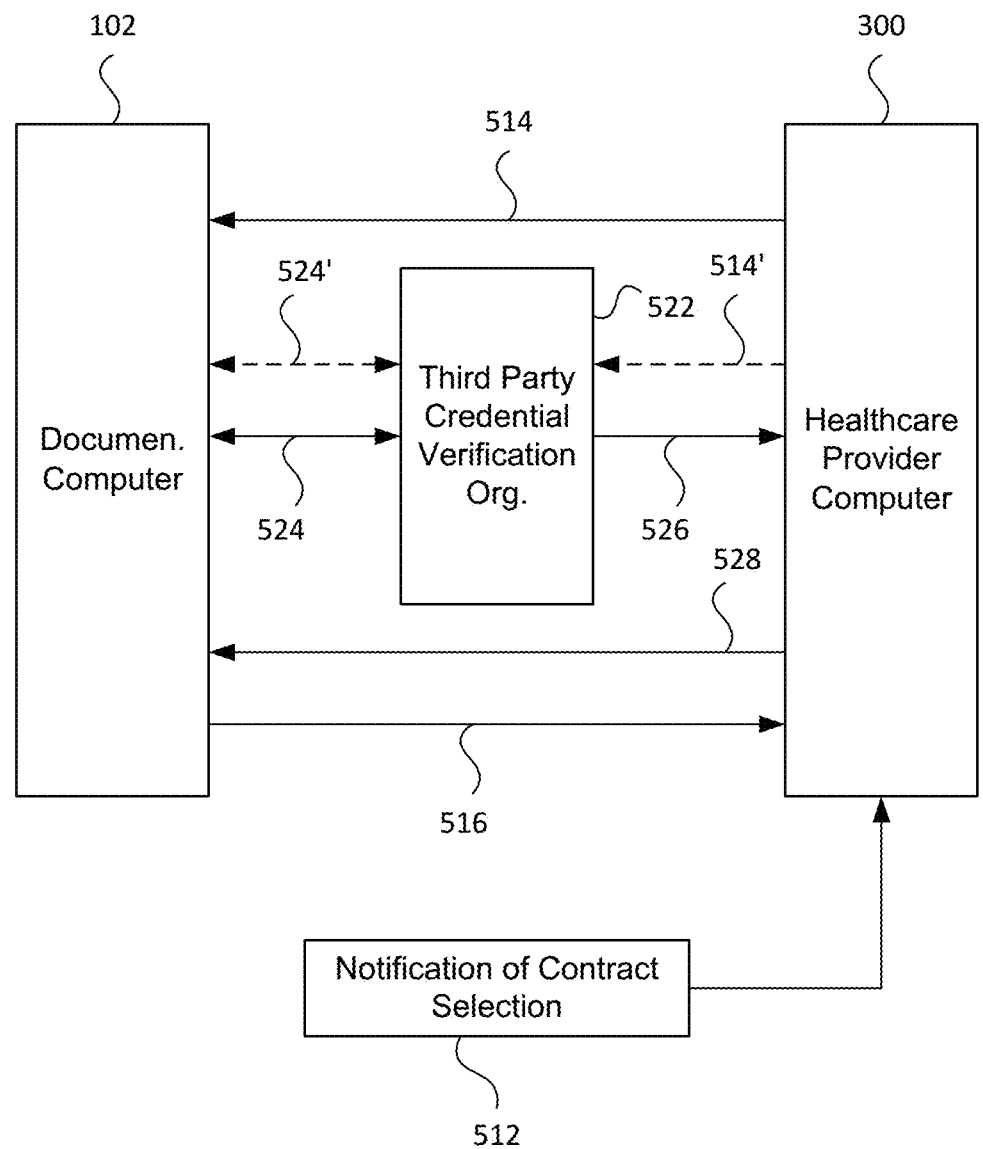
FIG. 3A is a block diagram expanding the functioning of the system according to FIG. 2.

Turning now to FIG. 3A, an expanded description of the process of validating the medical personnel data associated with the user. As discussed in connection with FIG. 2, once a contract selection is made, a notification of contract 512 selection is transmitted to healthcare provider computer 300. Healthcare provider computer 300 then sends a request to access medical personnel data associated with the user 514 that will include requests for specific data associated with the contract selected. The documentation computer 102 will allow access to the requested information if the user defined rules are satisfied. A third-party credential verification organization 522 is illustrated in FIG. 3A. The third-party credential verification organization 522 is an independent organization the healthcare provider can engage to verify the credentials of the user and may comprise one or more independent organizations. In one configuration, the request to access medical personnel data associated with the user 514 may include data instructing the documentation computer 102 to allow third party credential verification organization 522 to access the requested data 524. The third-party credential verification organization 522 will then perform the task of verifying the data provided and if verified, will then transmit a verification 526 to healthcare provider computer 300 that the data is verified and accurate. The healthcare provider computer 300 can then access the medical personnel data associated with the user 528, which will in turn be accessible 516 by healthcare provider computer 300.

Also depicted in FIG. 3A are dashed line arrows, which illustrate an alternative method of the verification process. For example, rather than sending the request to access medical personnel data associated with the user 514 to medical personnel records computer 102, a request 514' could be transmitted to third party credential verification organization 522, which in turn, requests access to the medical personnel data associated with the user 524'. This information is verified and the verification 526 is then transmitted to healthcare provider computer 300 that the data is verified and accurate.

Figure 3B:
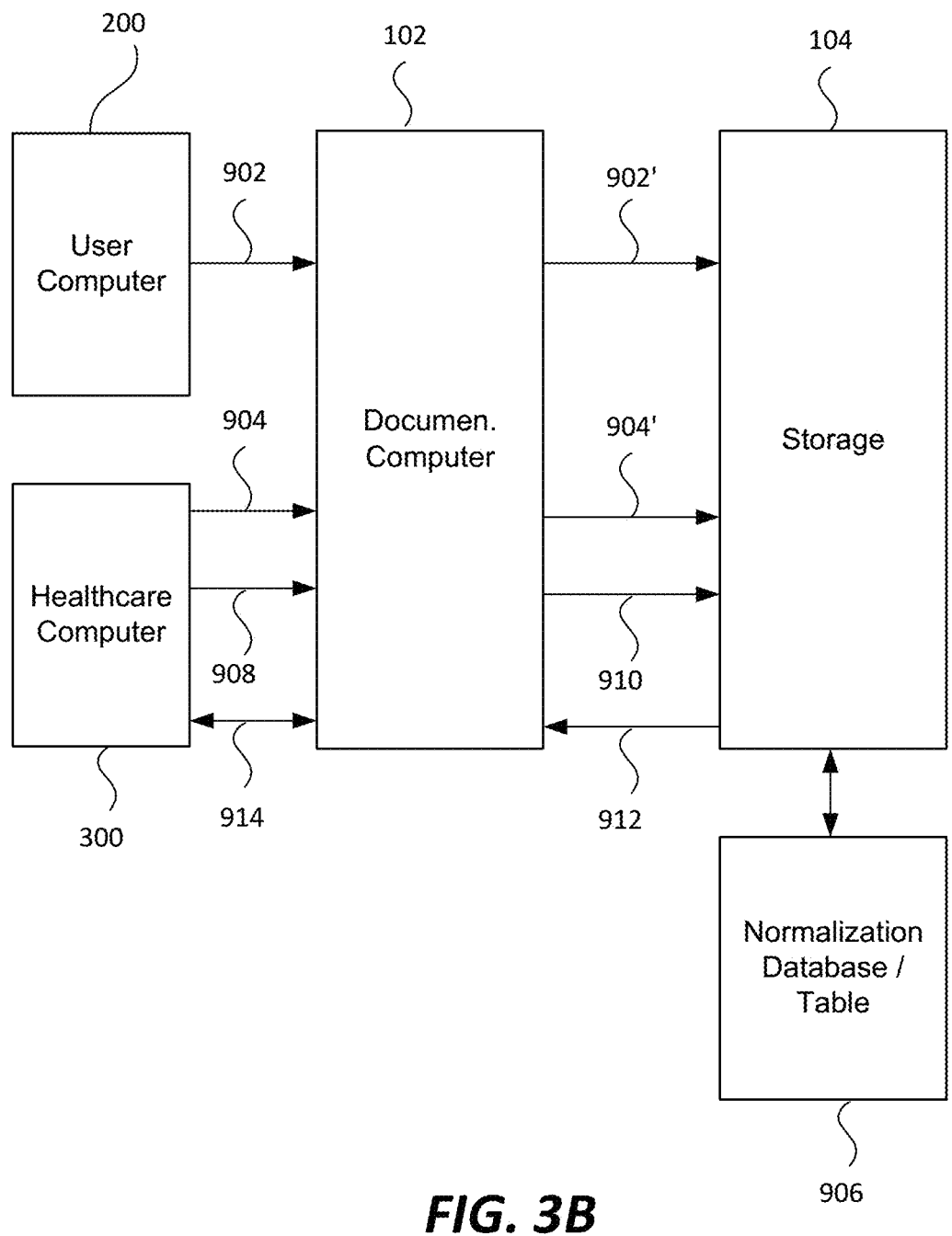
FIG. 3B is a block diagram illustrating an additional configuration for normalization of data provided by the user.

FIG. 3B is a functional information flow block diagram illustrating an additional configuration for normalization of the data provided by the user. In this configuration, a user submits user data 902 via a network connection with documentation computer 102 and saves 902' the user data on storage 104. Additionally, a healthcare computer 300 may provide data 904 relating to various information required by the healthcare provided to fill various healthcare positions, which is also saved 904' on storage 104.

The documentation computer 102 will then take the received data 902, 904 and normalize it with a normalization database/table 906 saved on storage 104 and accessible by documentation computer 102. This can be a challenge because not all information is provided as through data entry. Rather, some required information includes digital documents relating to certifications, school records, licenses, continuing education certificates, fellowship programs, immunization, physical exams, and on and on. All of these diverse digital documents may be in different formats or use different terminology from jurisdiction to jurisdiction so that they are not readily equivalent. Normalization is used to equate these diverse document and may include, for instance, equating terms used by the user and/or the healthcare provider with equivalent terms in the normalization database/table 906. This can be accomplished by the use of, for example, a lookup table where the software can automatically equate different terms. For example, in one jurisdiction a particular certificate (e.g., PALS) may be referred to or called by a first term, but in a second jurisdiction it may be referred to or called by a different term but is legally equivalent. In one configuration, meta data of a file may be appended with equivalent data from the lookup table allowing for ease of future look up and reference. In other instances, the file name may be altered, or an additional file may be generated that equates the file with other names. In any event, once a user uploads a PALS certification as is described in the example above, that file will be normalized to allow for identification of it by other names used in various jurisdictions. The same process can be followed for virtually all of the data submitted by the user providing their school certificates, state licenses and certifications, Federal certifications, personal identifying information and so on. It is contemplated that a healthcare provider will go through a similar normalization process when signing up with the documentation computer 102 such that its particular requirements and nomenclature are normalized by the normalization database/table 606. Accordingly, this is a process that would typically happen when signing up with the system, logging on and setting rules and requirements.

Accordingly, when a contract is selected and a third-party computer transmits the user and contract information to the healthcare provider computer 300, the healthcare provider computer 300 then requests 908 that certain information needed to qualify for a particular position described in a contract be made accessible by or be forwarded to the healthcare provider computer 300, which accesses the normalized information 910. The healthcare provider may then refer to those documents in nomenclature used by the healthcare provider and the documentation computer will be able to automatically identify and retrieve the information requested as the normalization would already have been done via appending of material to the meta data or changing of file names or creation of a file allowing for the quick identification of the information requested. If the user has set the rules governing access to the user data to allow the requested access by the healthcare provider computer 300, this data is retrieved 912 by the documentation computer 102 and either allows access to this data or transmits this data 914 based on the rules set up by the user governing the use of their data.

In this way, a user can simply provide documentation to the documentation computer 102 in the format they are accustomed to using, and the healthcare provider computer 300 can request and receive information automatically even if they are using nomenclature that differs from that used by the user. This provides a very easy user experience for all participants.

Not only has it become important to verify the identity of medical personnel, but it has also increasingly become important to verify the identity of healthcare providers. As stated previously, the verification of healthcare providers has increasingly become important as a proliferation of fraudulent jobs and providers has happened during the pandemic as the need for itinerate healthcare workers has increased. Seeing this demand and the nature of the internet has allowed unscrupulous individuals to pose as healthcare providers to lure healthcare workers into sharing their personal and medical credentialing information, which these fraudulent individuals use to steal the identities of the medical workers. As such, it has become important for medical workers to verify that the healthcare provider is, in fact, who they say they are and that jobs listed by that entity are, in fact, legitimate job listings.

Figure 3C:
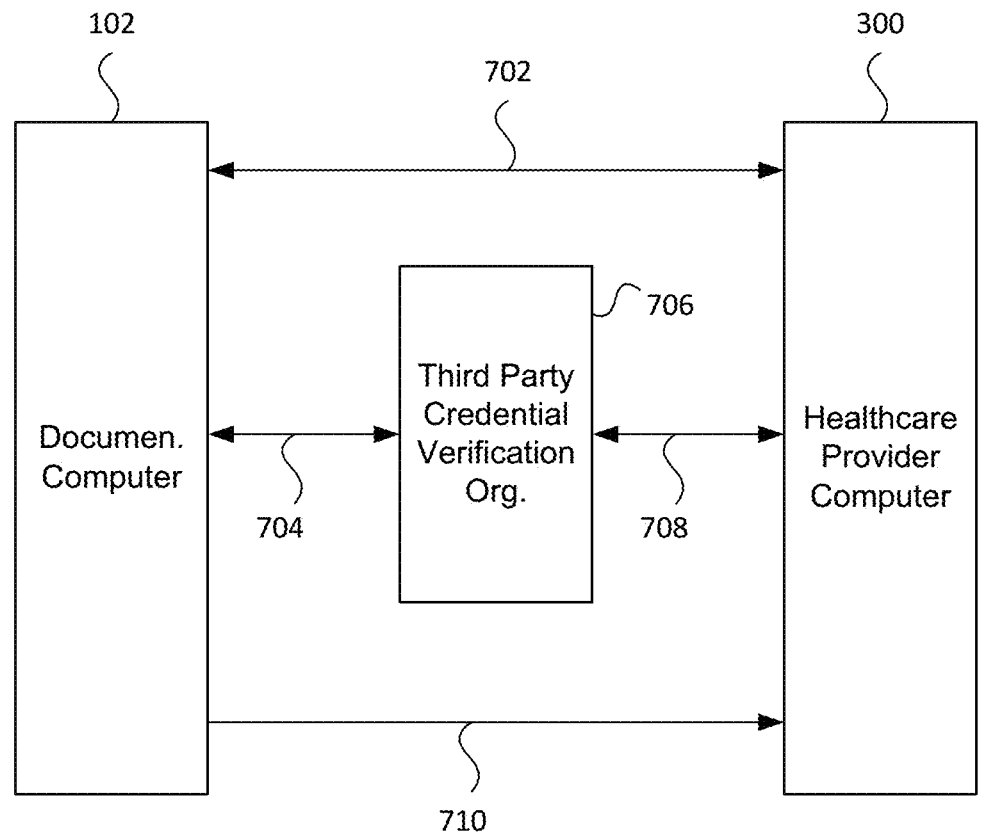
FIG. 3C is a block diagram illustrating a verification of a healthcare provider.

FIG. 3C is a functional information flow block diagram showing the verification of a healthcare provider. A healthcare provider has the option to sign up and register 702 with documentation computer 102. Documentation computer 102 then sets up the healthcare provider as a provider on documentation computer 102 and requests various information be provided by the healthcare provider. This can be accomplished by presenting a progressive series of windows to the operator to provide the relevant information such as, the name of the organization, the address, the contact information, the Tax ID number of the organization and any other information. It should be understood that various types of organizations other than healthcare providers can register with the system. For example, travel agencies, various Boards including medical, nursing and certification boards, insurance companies and so on. All of these can register and be accessible by the system. Turning back to the example of a healthcare provider, all of the relevant information needed to verify the identity of the provider would need to be uploaded including any facility licenses and insurance information, such as are used by hospitals. As the operators works through the series of widows or menus and fill out the data fields presented, verification of data 704 can be occurring in the background (e.g., verification of the tax ID number, verification of any license information or insurance information and so on), which can be accomplished by a third-party organization 706. During this process, it is possible that the third-party organization may require additional data be transmitted between the healthcare provider and the third-party organization 708. For example, an insurance company may request verification from the healthcare provider prior to transmitting any information to the documentation computer 102, or a certification organization may make a similar request. Once the operator has completed the registration process with documentation computer 102 and the information that has been provided by the organization has been verified, the documentation computer 102 can inform 710 the healthcare provider computer 300 that they have successfully registered and have been verified.

It should be noted that once a healthcare provider has registered, they have the opportunity to set up virtual filing cabinet for access to the records of each of their employees in the system. For example, the healthcare provider is able to create a File Tab for those going through the credentialing process allowing the healthcare provider to actively monitor various information including certifications and licenses to ensure they are up-to-date and not expired. The medical worker in turn, can set up a virtual briefcase to share with the healthcare provider. This is especially helpful for itinerate medical workers who may only be at a job with the healthcare provider for discrete periods of time. Based on the rules set up by the user to allow access to their medical information, a healthcare provider can open the virtual briefcase when allowed by the user. It is contemplated that the user may only give the healthcare provider access to certain documents for a certain length of time. However, the virtual filing cabinet including a tab for the worker may allow the healthcare provider to include the workers name, assign them an ID and include other general information about the worker. It is contemplated that sensitive records including for example, the workers SSN, license nos., certification nos. and so on, will only be accessible based on the rules put in place by the user.

Another feature of the virtual file is that it enables a healthcare provider to have direct encrypted communication with a user via the system 100. These communications could be between employer and employees, contractors, students, and residents; including third-party companies, surgical centers, medical offices and hospitals.

Figure 4:
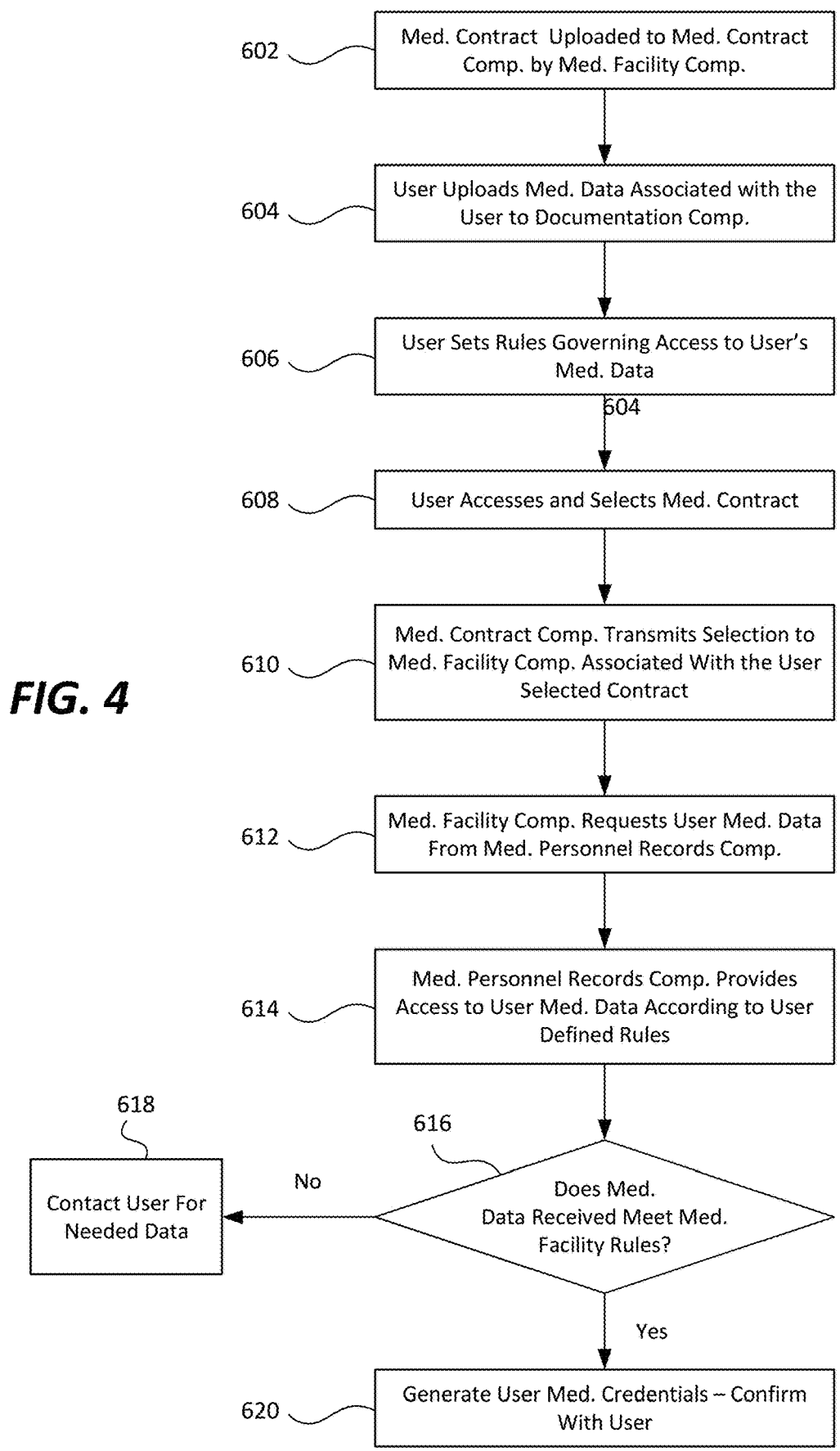
FIG. 4 is a flow diagram according to FIG. 1.

Turning now to FIG. 4, a flow and decision diagram is provided illustrating the processes followed by the system 100 in one configuration.

Initially a Medical Contract is Uploaded to Medical Contract Computer by a Healthcare provider Computer 602. A User Uploads Medical Data Associated with the User to Documentation Computer 604. Additionally, the User Sets Rules Governing Access to User's Medical Data 606. Once these preliminary steps are completed, the User Accesses and Selects a Medical Contract 608. From that point, the Medical Contract Computer proceeds to Transmit the Selection to a Healthcare provider Computer Associated With the User Selected Contract 610.

The method then advances to the step of the Healthcare provider Computer Requests User Medical Data From Documentation Computer 612. The Documentation Computer will then Provide Access to the User Medical Data According to User Defined Rules 614. The verification of the information provided and described in connection with FIGS. 3 and 3A may occur at this point. Assuming the information is verified and acceptable, the system will then determine whether Medical Data Received Meets the Healthcare provider Rules 616. If not, the system will proceed to Contact the User for Needed Data 618. If the data does meet the Healthcare provider rules, the system proceeds to the step of Generate User Medical Credentials—Confirm With User 620.

A major advantage of the present system and method of allowing access to itinerate medical workers personal data is the increased security. Previous methods include the transmission of data via email or the like without any ability to automatically adjust the data provided to meet the needs of the healthcare provider. Likewise, the restriction of access is controlled by the user as the data is allowed to be accessed for only a certain period of time while the data is verified and then automatically provides for the generation of verified credentials. The data is not saved on the healthcare provider computer and cannot be accessed after a specified period of time. As such, even if a data breach were to occur at the healthcare provider, the opportunity for the user's data to be compromised is very small.

It is contemplated that upon user registration with the medical personnel records computer 102, a "Terms and Conditions" agreement will be executed by the user. In addition, a "Privacy" agreement will be signed by user at the time their unique links are created, but before they are sent. The links may, in one configuration, be generated by the user having a lifespan chosen by the user. The duration the system links will be active can vary, but may be in one embodiment, selected from 24 to 72 hours. It is, however, contemplated that virtually any length of time may be selected. The links provided may require a password to be accessed. The application allows for the user to create a profile and follows a common flow of documentation needed for credentialing.

As an additional feature, once all the user's information has been entered and saved to the storage 104, the user will have the option to create a Curriculum Vitae (CV) which can be included with the uploaded forms that will be sent to a recipient healthcare provider.

It should be noted that, while various functions and methods have been described and presented in a sequence of steps, the sequence has been provided merely as an illustration of one advantageous embodiment, and that it is not necessary to perform these functions in the specific order illustrated. It is further contemplated that any of these steps may be moved and/or combined relative to any of the other steps. In addition, it is still further contemplated that it may be advantageous, depending upon the application, to utilize all or any portion of the functions described herein.

FIGS. 5-13 are illustrated screen shots of some of the webpages on the medical personnel records computer 102 that can be used to upload personal medical information associated with the user.

Figure 5:
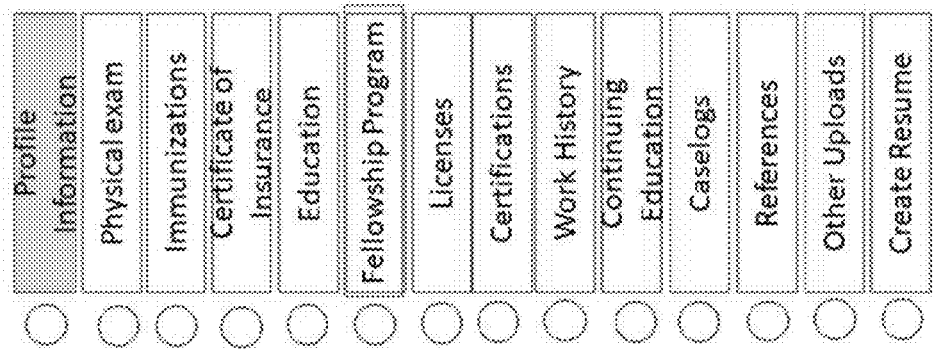

FIG. 5 illustrates a menu of options where Profile Information has been selected. The webpage allows for the input of the user's name, address, profile information and passport picture. All of this information is required for medical credentialing.

FIG. 6 illustrates a menu of options where Physical Examination has been selected. There are various formats that this information can be provided in, including for example, a text format or an image format.

Figure 7:
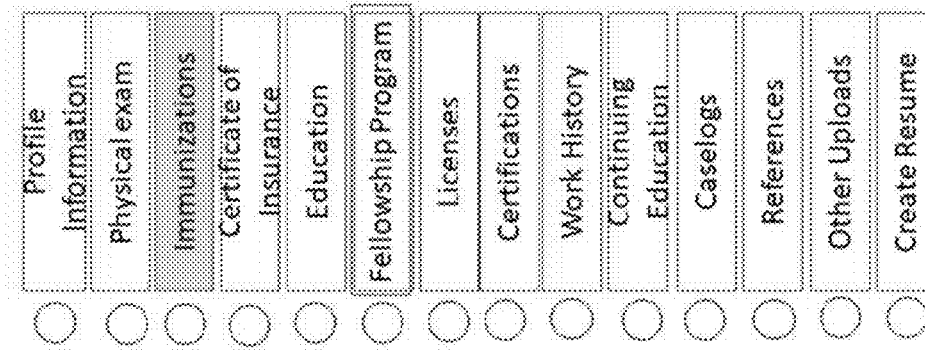

FIG. 7 illustrates a menu of options where Immunization Information has been selected. This information could include for example, Titers, Flu Shot, PPD and other immunization records.

Figure 8:
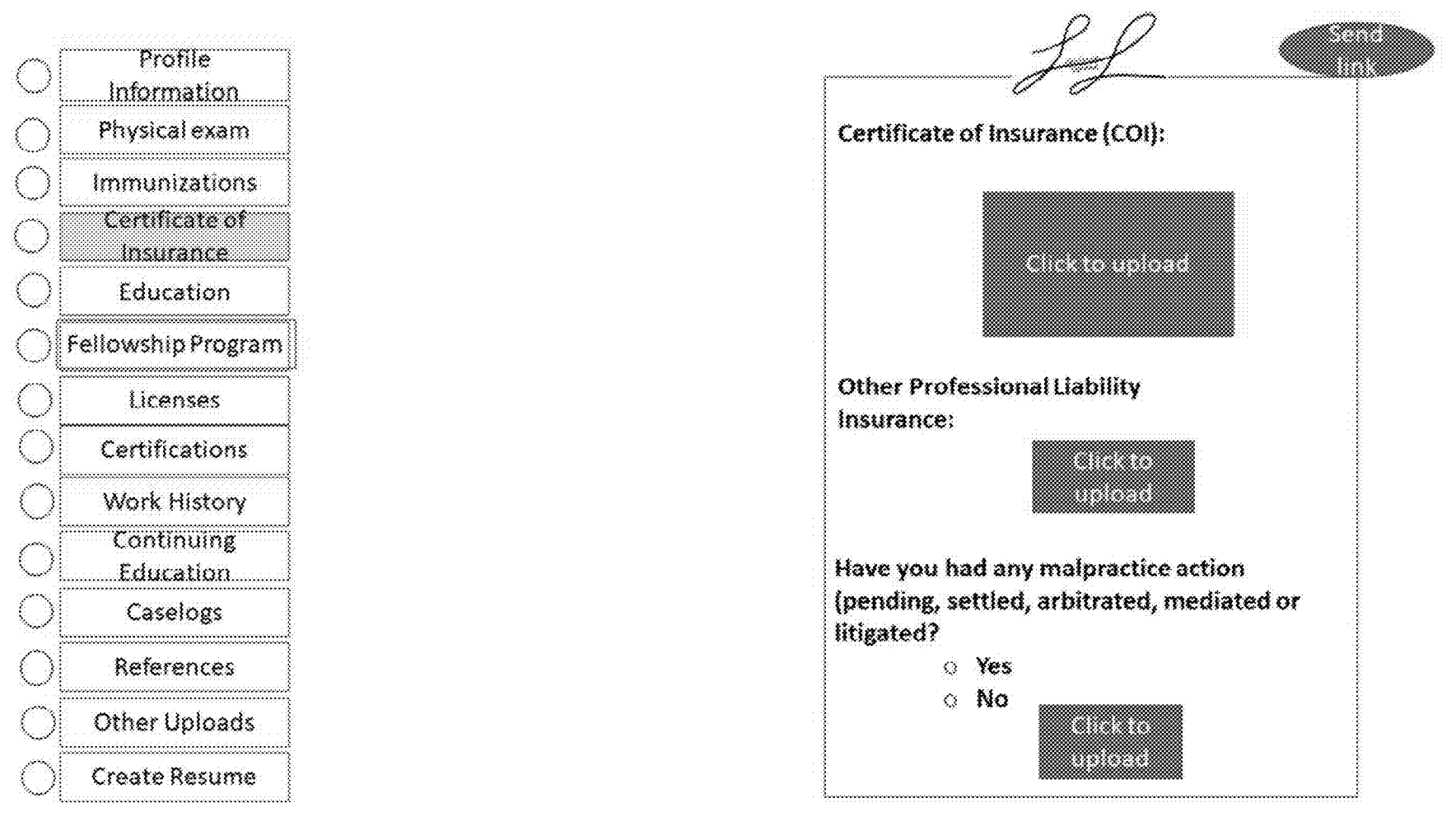

FIG. 8 illustrates a menu of options where Certificate of Insurance has been selected. This information could include for example, malpractice insurance including letters of verification, liability insurance, and data relating to insurance claims and the like.

Figure 9:
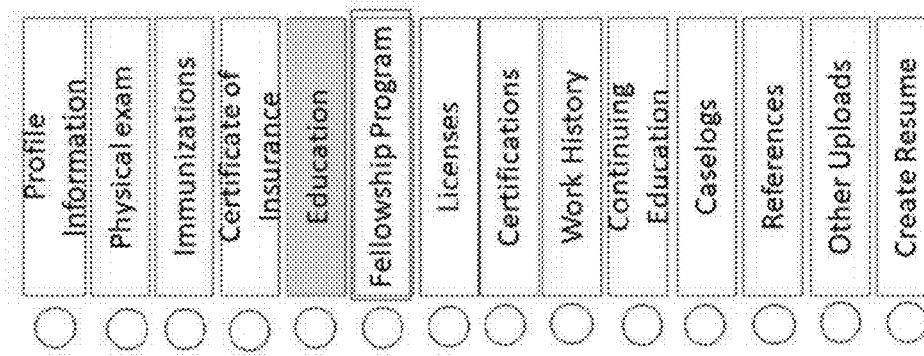

FIG. 9 illustrates a menu of options where Education History has been selected. This information could include for example, undergraduate transcripts including a copy of the undergraduate diploma, graduate transcripts including a copy of the graduate diploma, fellowship training, and the like.

Figure 10:
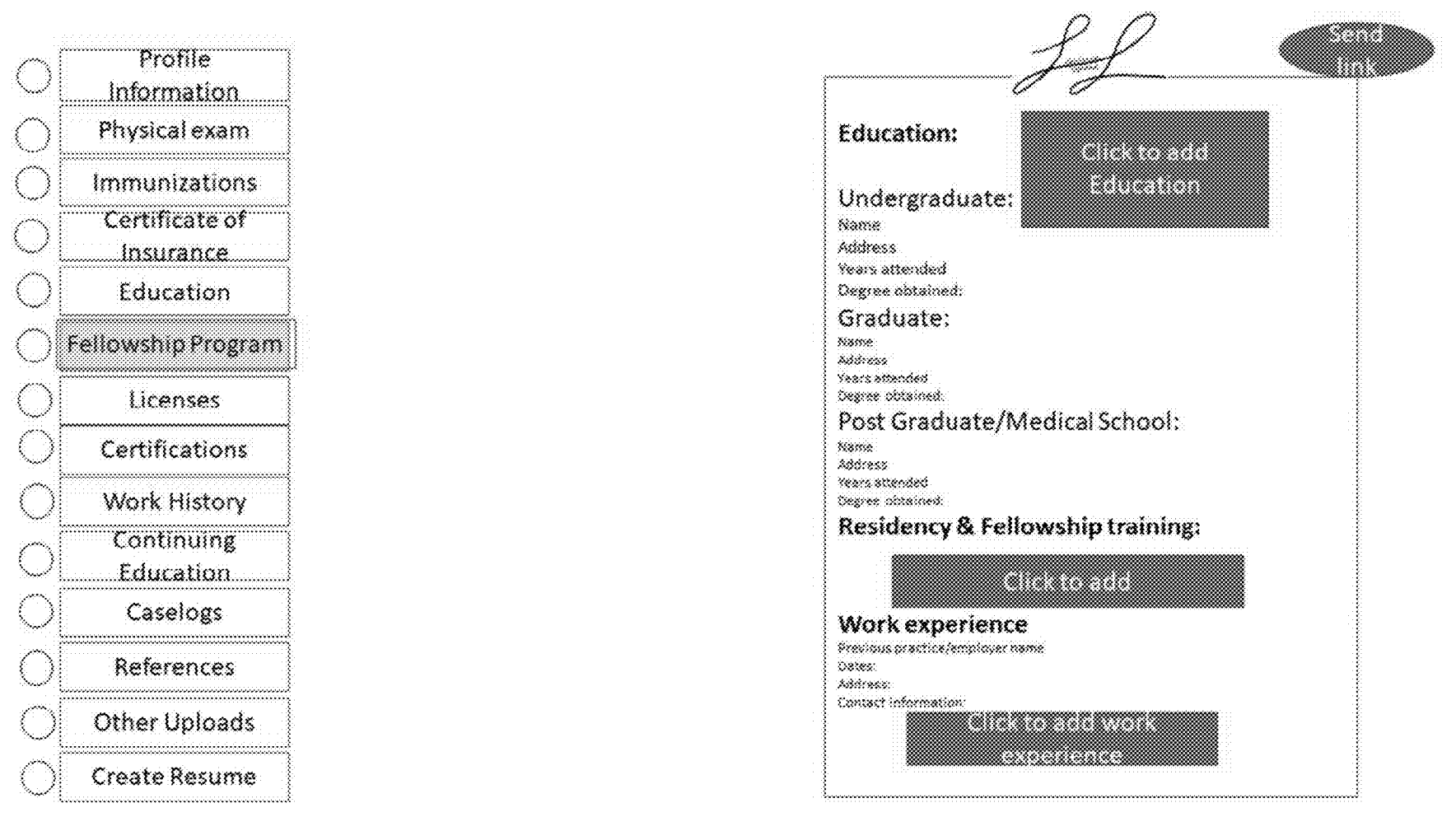

FIG. 10 illustrates a menu of options where Fellowship/Residency has been selected. This information could comprise any and all information showing completion of any fellowships and/or residency.

Figure 11:
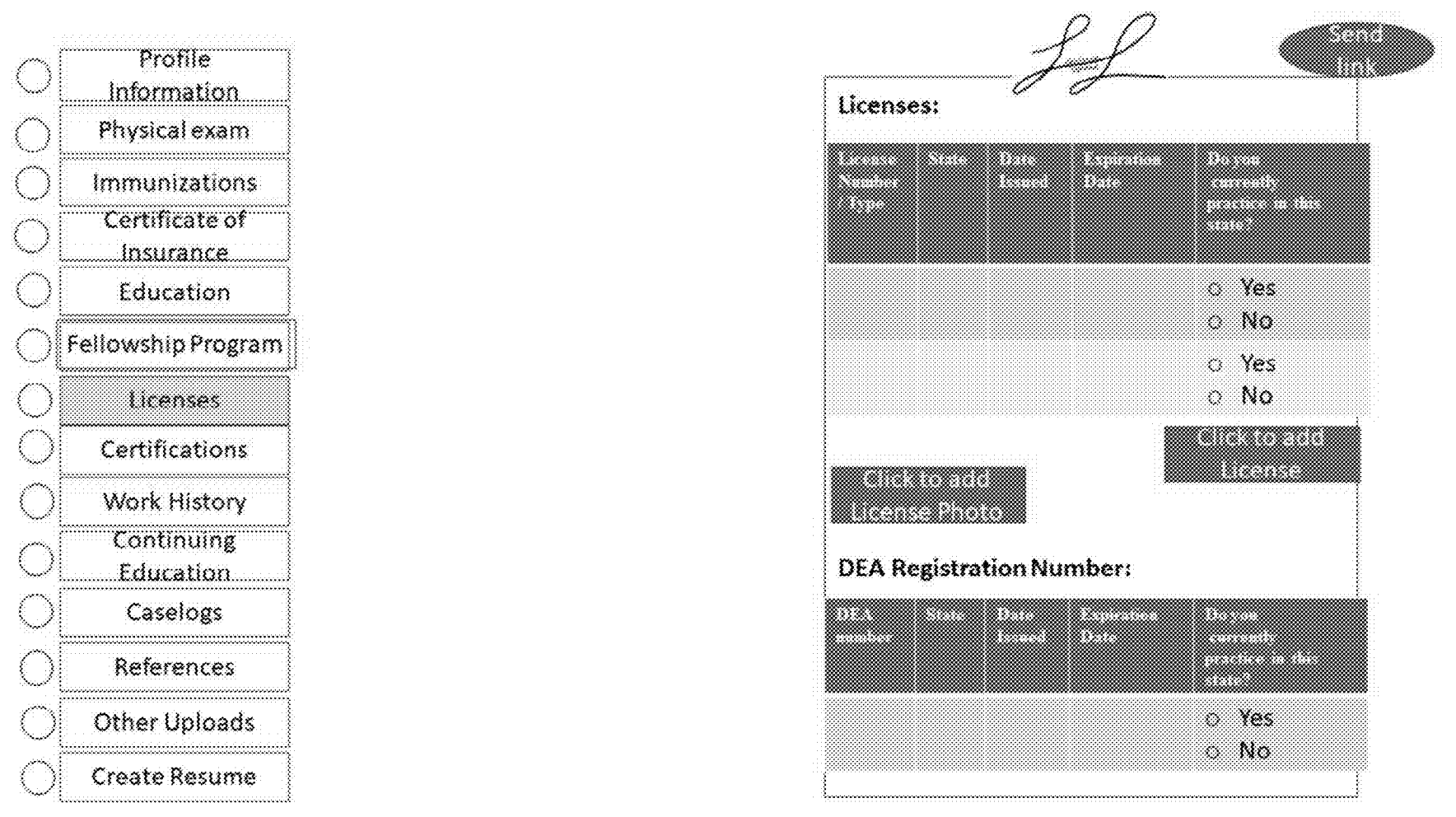

FIG. 11 illustrates a menu of options where Licenses has been selected. This information could include a listing of all medical licenses listed by state and including the license number, the year issued and the expiration date.

FIG. 12 illustrates a menu of options where Certifications has been selected. This information could include among other certifications, Advanced Cardiac Life Support (ACLS), Pediatric Advanced Life Support (PALS), Basic Life Support (BLS), Neonatal Resuscitation Program (NRP), various Trauma certifications, Board Certification/Membership Cards and any other certifications.

FIG. 13 illustrates a menu of options where Work History has been selected. This information could quite lengthy including the facility name, date of employment, address for the healthcare provider and contact information. It is contemplated that as work contracts are accepted and completed, the system could automatically update this section for the user. For example, at the date of completion of the work contract or at another date (e.g. when the user logs back into medical personnel records computer 102) the system could automatically prompt the user as to whether the contract was successfully completed and whether the user's work history should be updated. Upon confirmation, the system could enter all the information from the previous work contract, which could be received from the medical contracts computer 400 or from the healthcare provider computer 300.

Other screens could include for example, Continuing Education information, Case logs information, and Reference information. The above are provided to further illustrate the type of information the user may provide to medical personnel records computer 102 and may want to be received by healthcare provider computer 300 prior to generating credentials to fulfill a selected contract.

Additionally, once all of the user's information has been entered into the system 100, the user has the option to create a Curriculum Vitae (CV), which can be included with the uploaded forms that will be sent to the recipient and would be assembled based on the information provided by the user. Additionally, it is contemplated that the resume builder application could automatically update and continue building the user's resume as various work contracts are selected and fulfilled.

Figure 14:
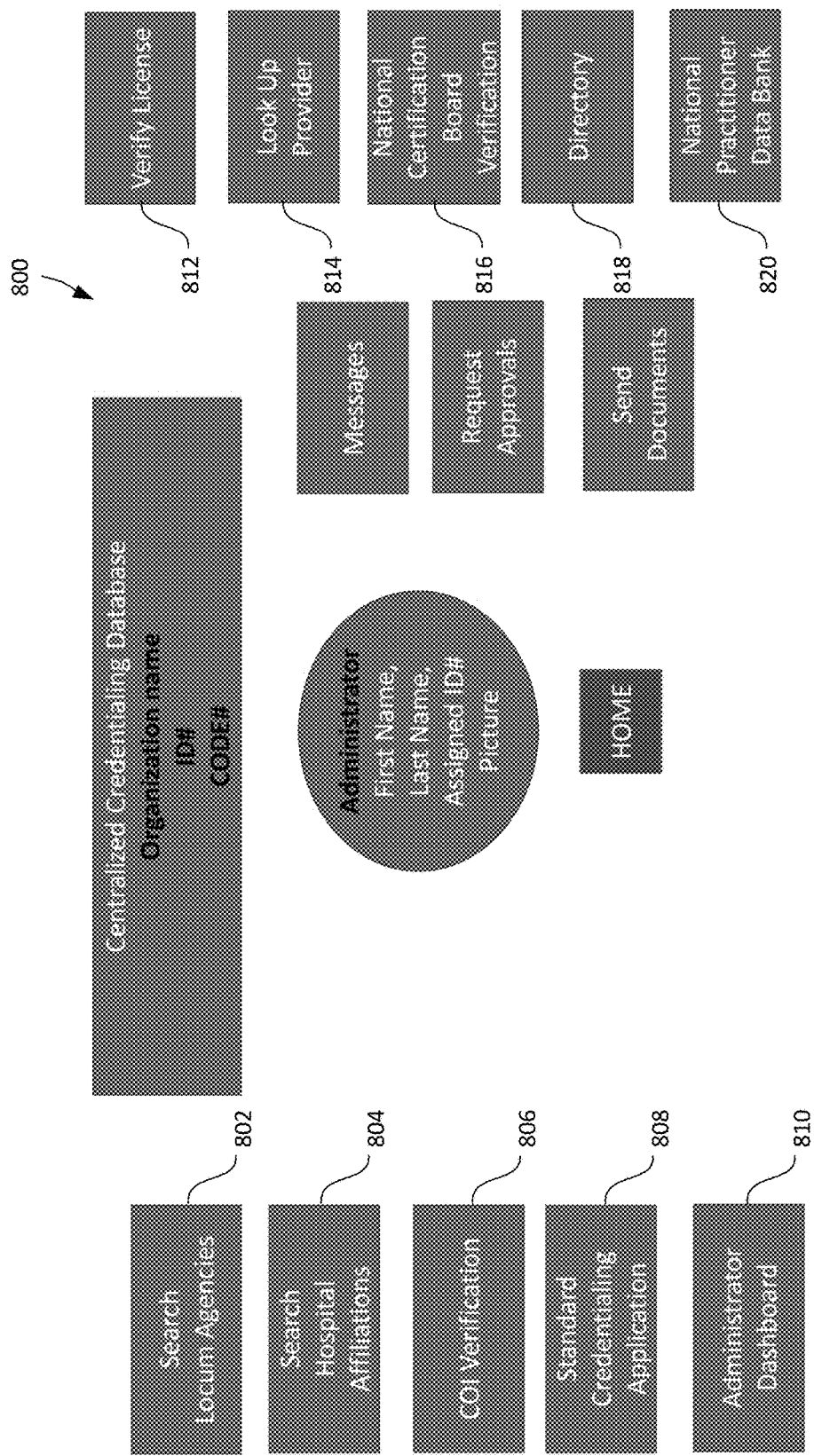

FIG. 14 is a screen shot of the home page 800 after login to the Centralized Credentialing Database. Various features are displayed on the home page including Search Locum Agencies 802, Search Hospital Affiliations 804, COI Verification 806, Standard Credentialing Application 808, Administrator Dashboard 810, Verify License 812, Look up Provider 814, National Certification Board Verification 816, Directory 818, National Practitioner Data Bank 820 and others.

Figure 15:
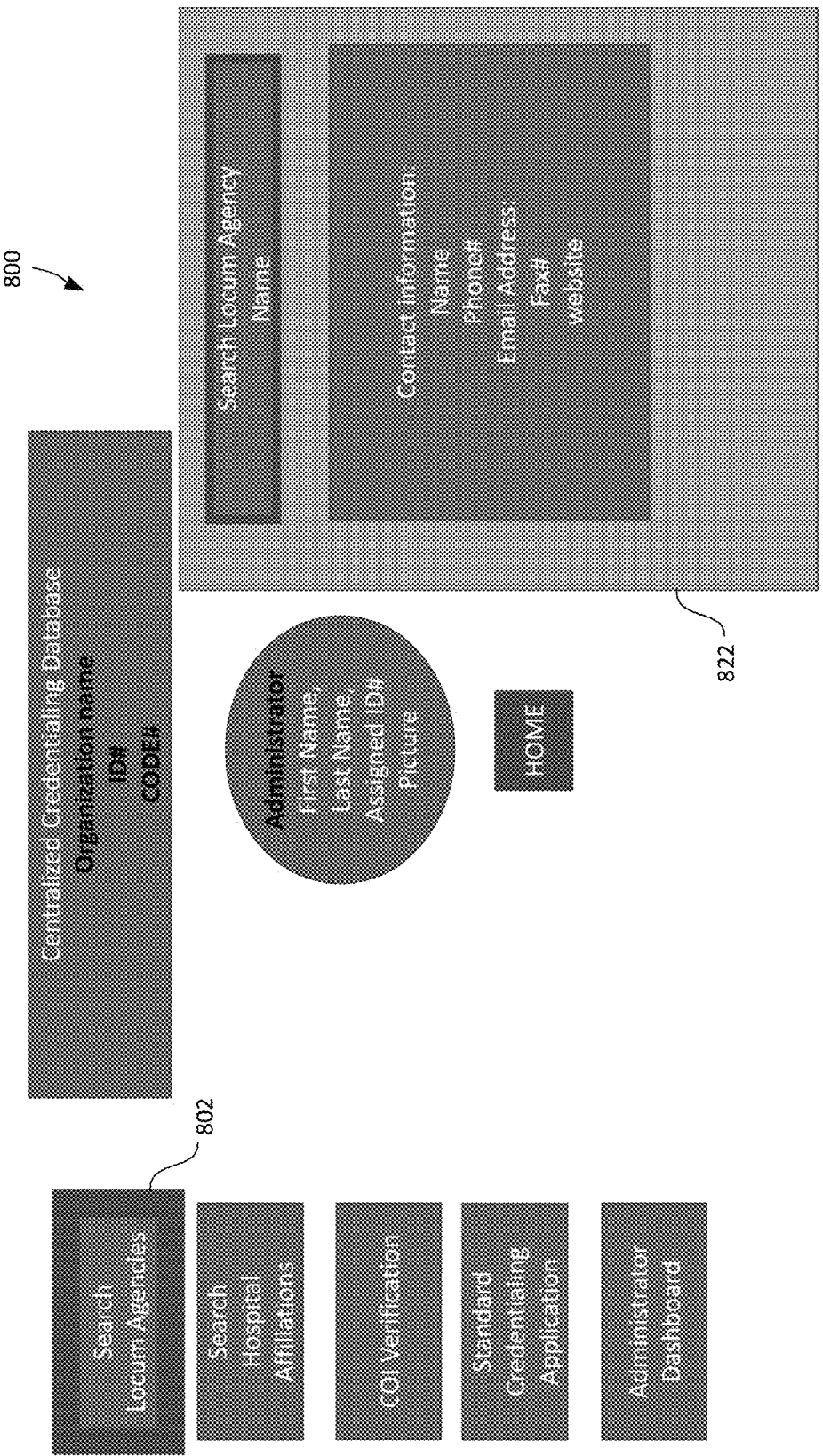

FIG. 15 shows when the button Search Locom Agencies 802 has been selected and the various information that is displayed in information window 822. In this instance, searching by name allows for various information to be displayed relating to that agency. Alternatively, providing certain information (e.g., contact information) could allow for identification of the agency.

Figure 16:
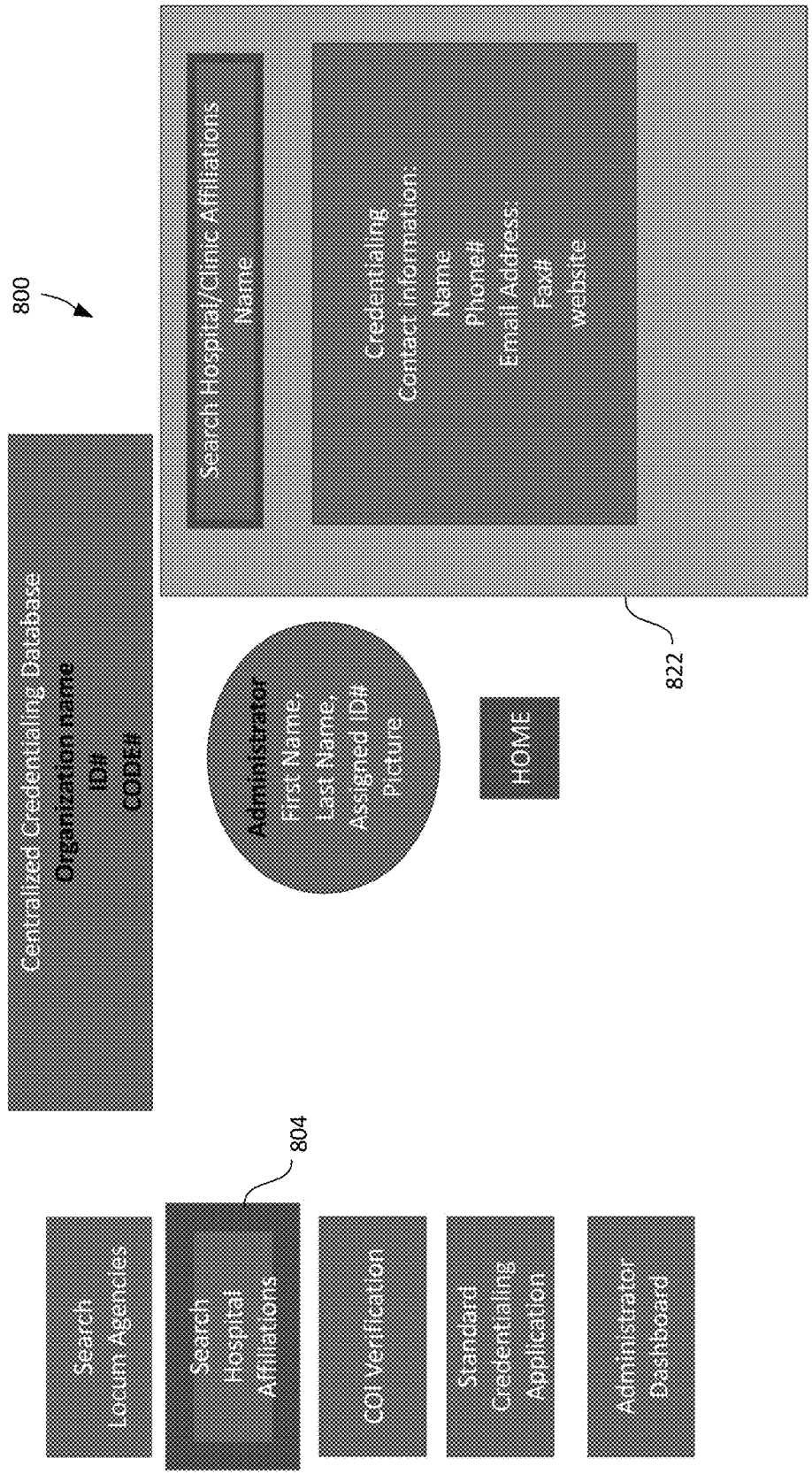

FIG. 16 shows when the button Search Hospital Affiliations 804 has been selected and again, various information that is displayed in information window 822. This allows for searching of hospital and clinical affiliations.

Figure 17:
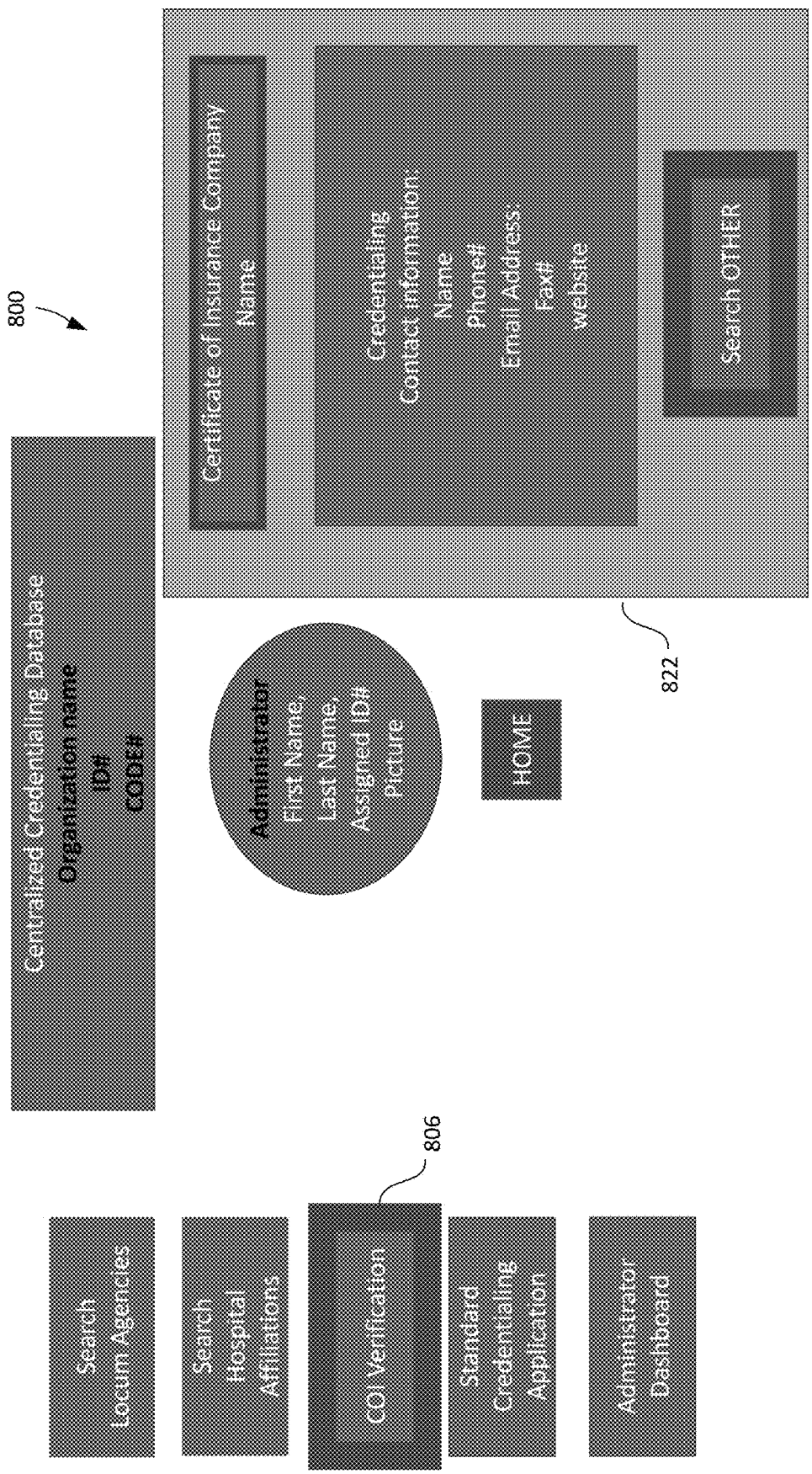

FIG. 17 shows when the button COI Verification 806 has been selected. Various information is displayed in information window 822 relating to the Certificate of Insurance that may be associated with an institution, a user, a healthcare provider and so on. This allows for identifying the relevant contact information relating to the insurance.

Figure 18:
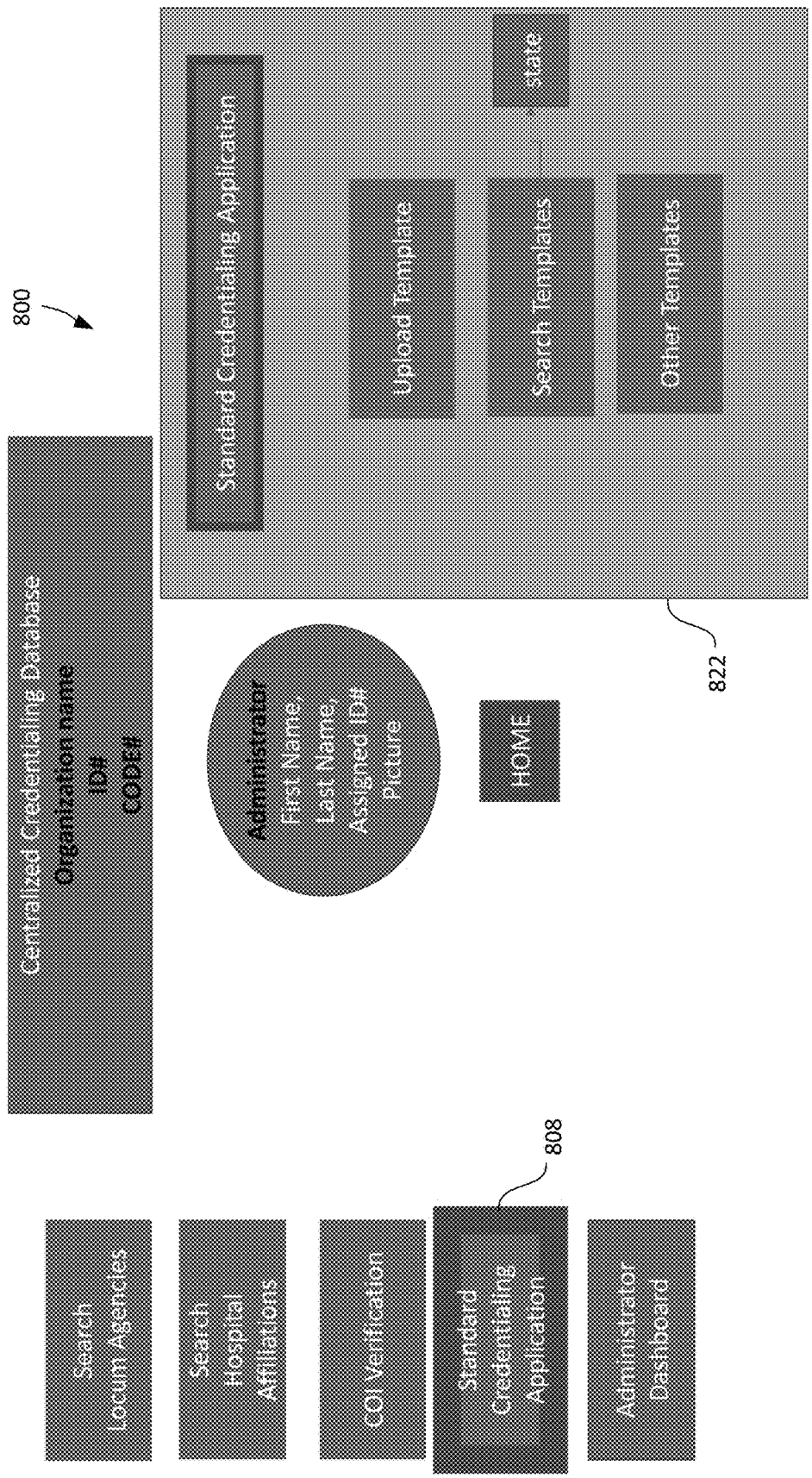

FIG. 18 shows when the button Standard Credentialing Application 808 has been selected. Various information is displayed in information window 822 relating to the credentialing application including, for example, the various templates used in the process.

Figure 19:
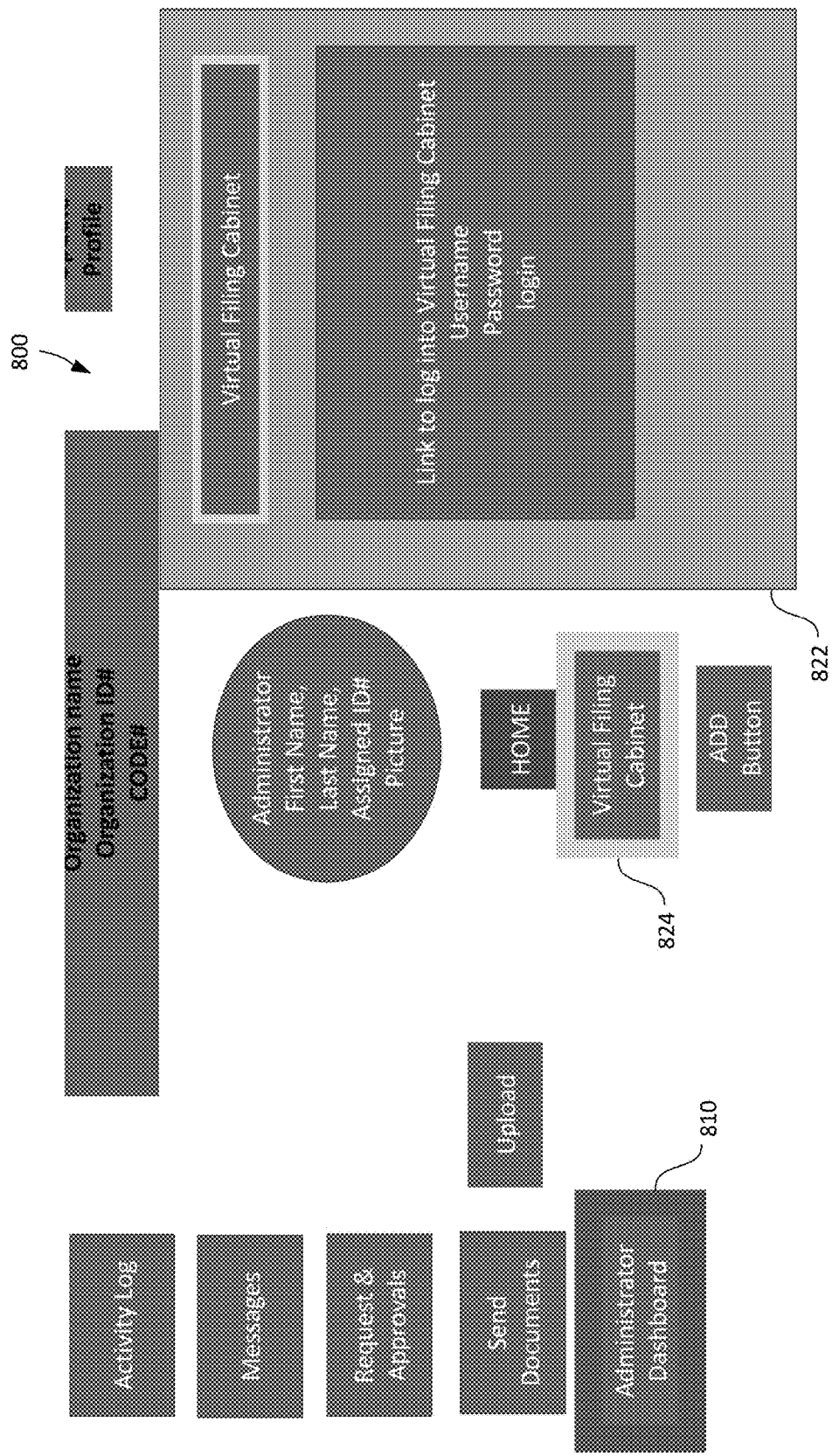

FIG. 19 shows when the button Administrator Dashboard 810 has been selected and the Virtual Filing Cabinet 824 has been selected. Virtual filing cabinet information is displayed in information window 822 relating to select medical workers for a healthcare provider. In this way, a healthcare provider can maintain specific records relating to a medical worker, however, they will only be able to access the sensitive medical records for the medical worker based on the rules defined by the user.

Figure 20:
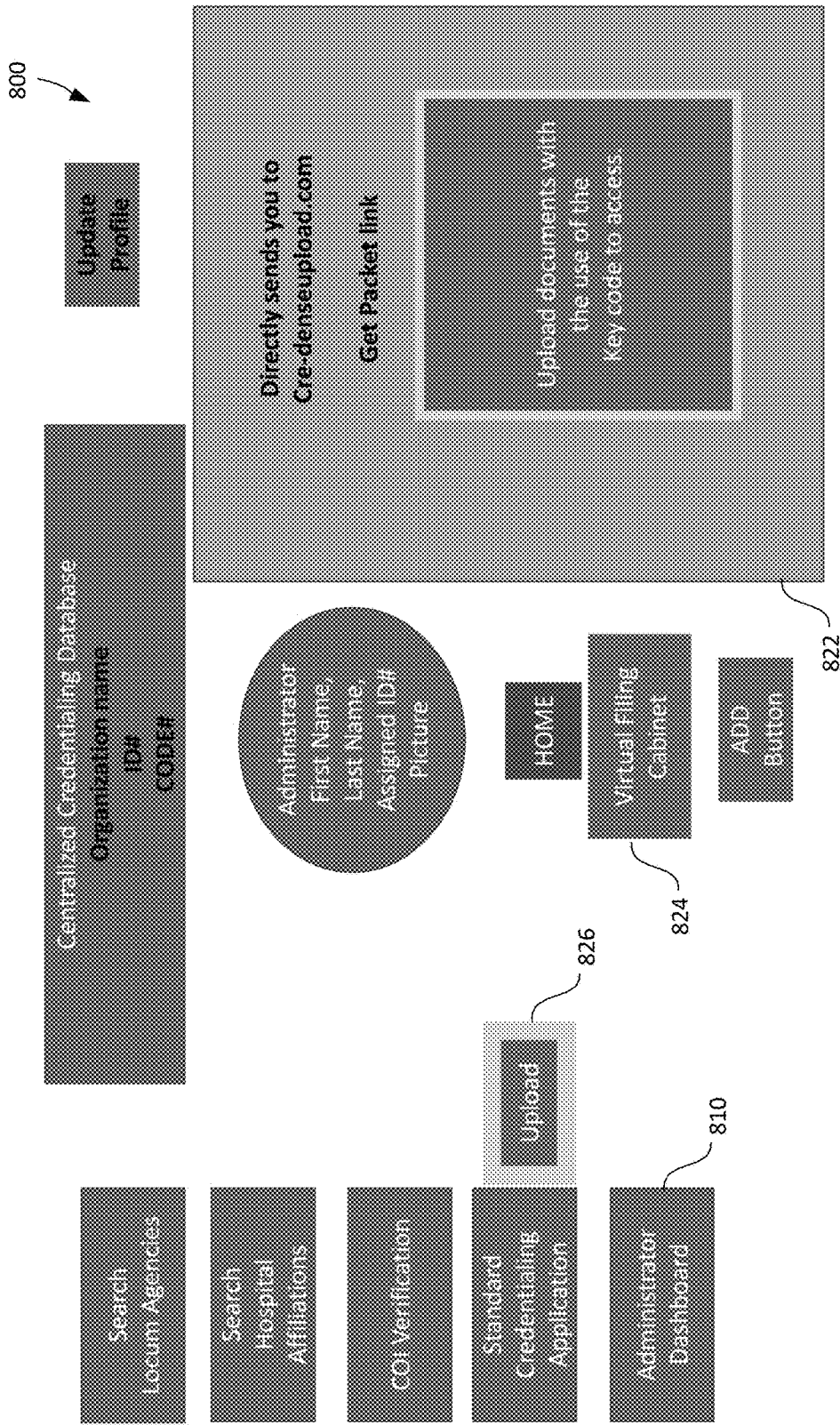

FIG. 20 shows further functionality of the Administrator Dashboard 810 providing an upload 826 button that allows for documents to be uploaded as shown in window 822.

Figure 21:
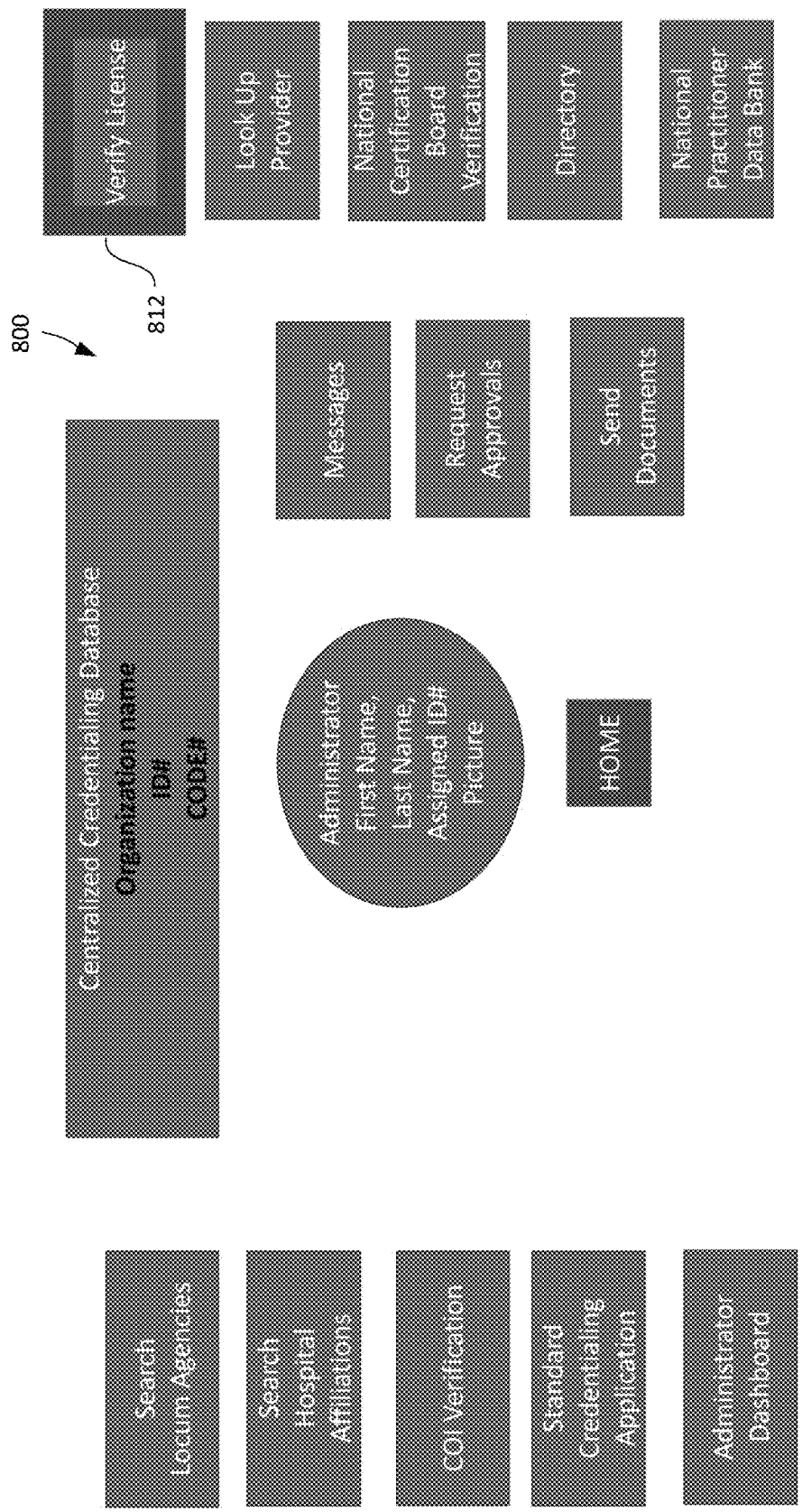
Figure 23:
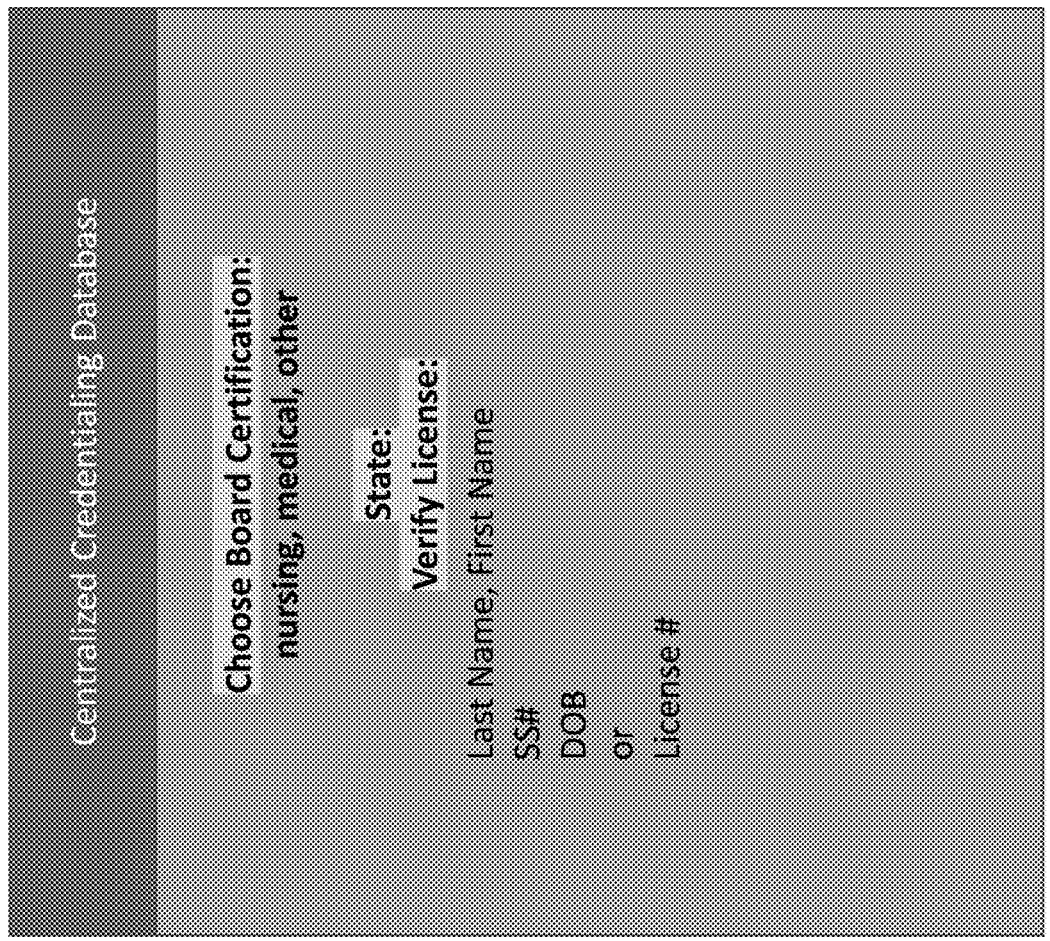

FIGS. 21-23 show when the button Verify License 812 has been selected. FIG. 21 shows the Verify License 812 button being selected, and FIG. 22 shows the screen that various selections of what institutions you are seeking to verify a medical license. FIG. 23 shows the screen where specific information can be input into the system for verification of a specific medical license.

Figure 24:
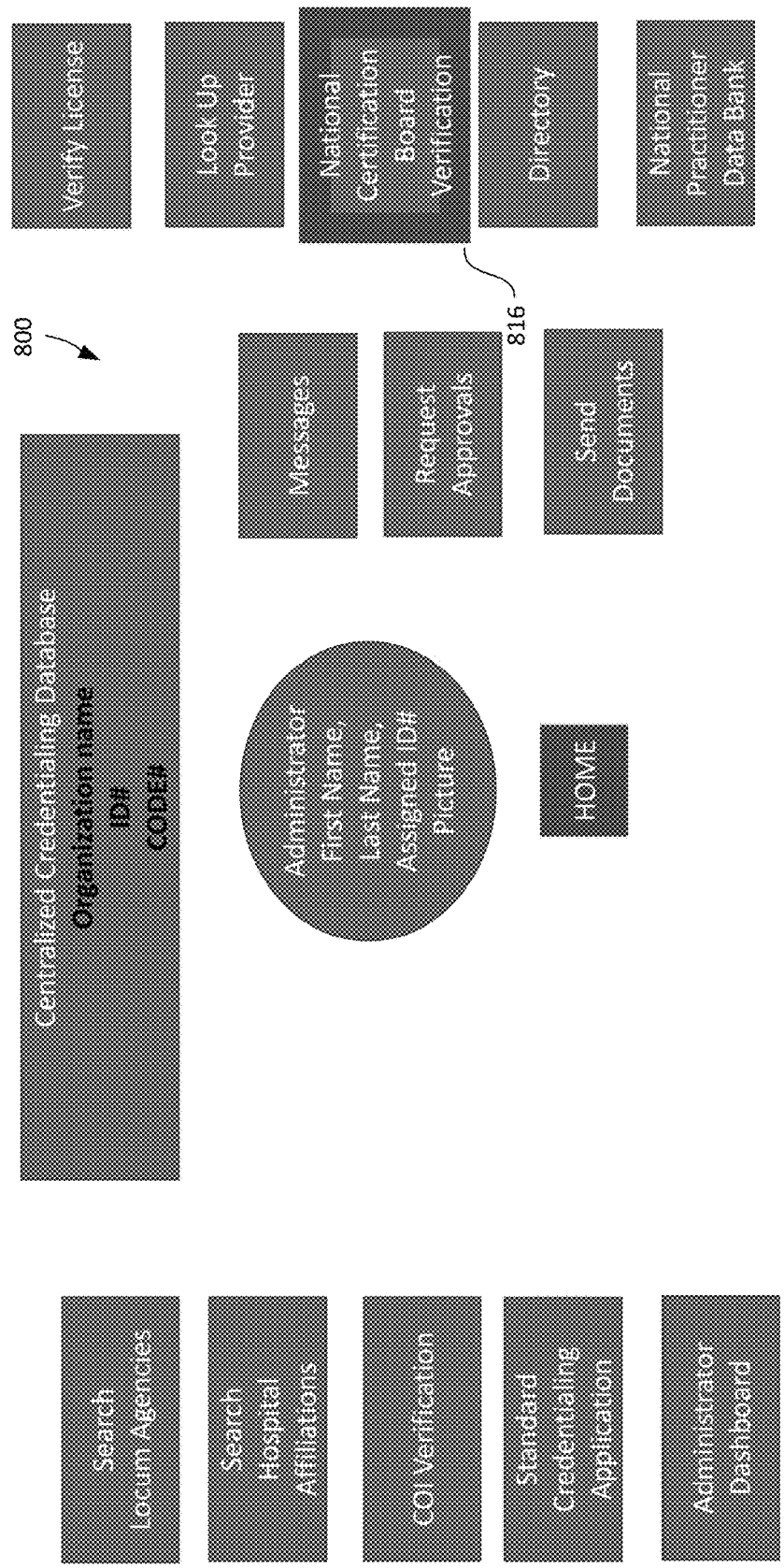
Figure 25:
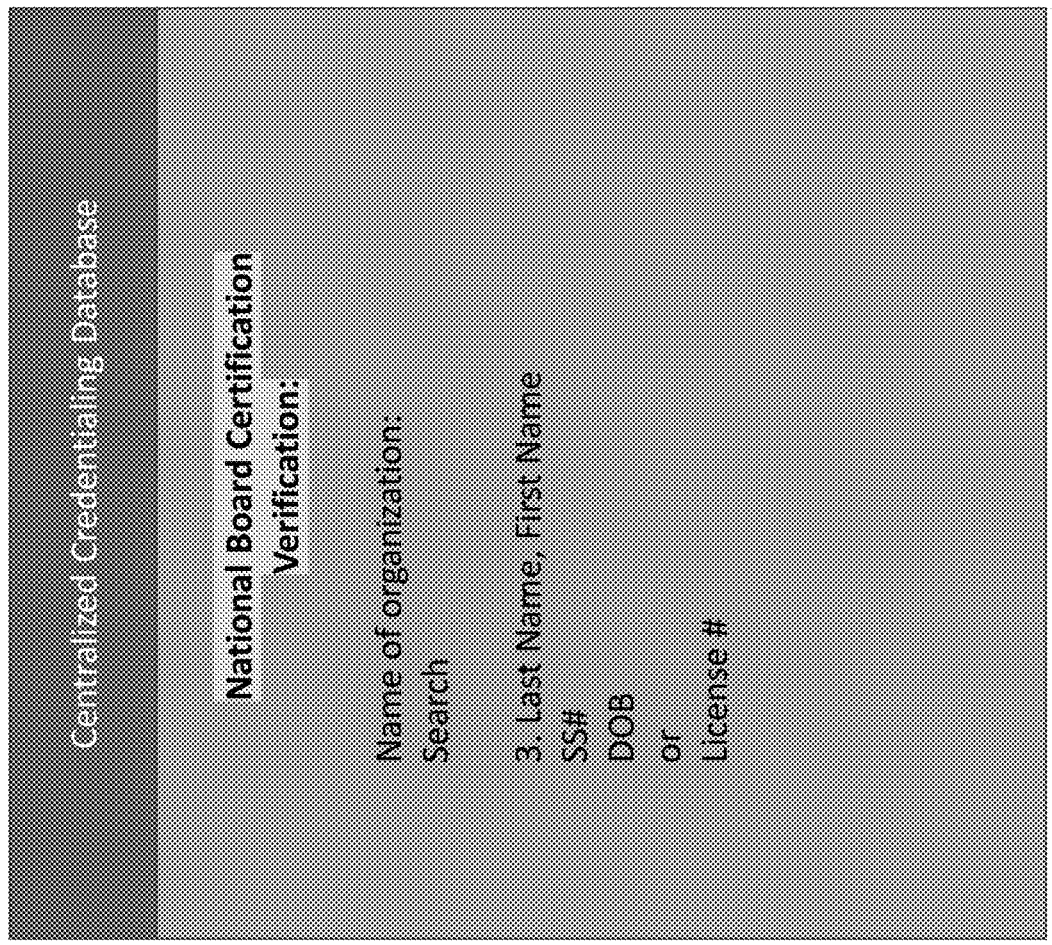

FIGS. 24-25 when the button Verify License 812 has been selected. FIG. 24 shows the National Certification Board Verification 816 button being selected, and FIG. 25 shows the screen where specific information can be input into the system for verification of a specific medical certification.

It will be understood by those of skill in the art that certificate based encryption technology may be used for all communications between the various computer systems. For example, communications between the documentation computer 102 and the healthcare provider computer 300; between the documentation computer 102 and medical contracts computer 400; between the documentation computer 102 and user computer 200; and between the documentation computer 102 and any computer used by a third-party verifying any information saved to the documentation computer 102.

Likewise, while the method of appending data to the meta data of a file may be a preferred method for normalization of data saved on the system, it is understood that there are many ways of saving data to a file that can be accessed during a search allowing for that file to be associated with a term(s) for ease of identification. Any such method of appending or associating data with digital documents uploaded to the system which are then normalized are contemplated by the invention.

Although the invention has been described with reference to a particular arrangement of parts, features and the like, these are not intended to exhaust all possible arrangements or features, and indeed many other modifications and variations will be ascertainable to those of skill in the art.

What is claimed is:

1. A system for processing medical personnel data of a user comprising:
   a documentation computer having a storage and coupled to a network;
   said documentation computer receiving from a medical personnel user computer, medical personnel user personal information;
   said documentation computer verifying the medical personnel user personal information by communication with a third-party computer to verify the authenticity of the medical personnel user personal information, and thereafter registering the medical personnel user as a validated registered medical personnel user of the system;
   said documentation computer receiving from a medical personnel user computer, medical personnel digital documents associated with the medical personnel user and data associated with the medical personnel digital documents, the documentation computer normalizing the data associated with the medical personnel digital documents to create normalized data associated with the medical personnel digital documents, the documentation computer saving the medical personnel digital documents and the normalized data on the storage;
   said system receiving from the medical personnel user instructions defining a set of rules governing access to the medical personnel digital documents and data associated with the user including a defined time period for access to the medical personnel digital documents and data associated with the medical personnel medical personnel user;
   said system saving the data associated with the medical personnel user and the set of rules governing access to the data associated with the medical personnel user on the storage;
   said system receiving healthcare provider data from a healthcare provider computer, verifying the healthcare provider data by communication with a third-party computer to verify the authenticity of the healthcare provider data, and thereafter registering the healthcare provider as a validated registered healthcare provider user of the system;
   said medical personnel user accessing a medical contract computer with the medical personnel user computer, the medical contract computer having at least one medical contract associated with the healthcare provider;
   wherein upon selection of the at least one medical contract, the medical contract computer transmits information relating to the medical personnel user and the medical contract to the documentation computer;

said documentation computer selectively allowing a healthcare provider computer associated with the at least one medical contract to access to the digital documents and the normalized data associated with the medical personnel user for the defined time period and according to the user defined rules;

said documentation computer presenting at least some of the digital documents and the normalized data associated with the medical personnel user to the healthcare provider computer for the defined time period based on parameters defined by the healthcare provider computer and based on the user defined rules.

2. The system according to claim 1, wherein the digital documents are selected from the group consisting of: certifications, school records, licenses, insurance documentation, continuing education certificates, fellowship program documentation, immunization records, physical exam records, malpractice records and combinations thereof.

3. The system according to claim 2, wherein when said documentation computer normalizes the data associated with the digital documents based on a set of rules saved on the storage.

4. The system according to claim 3, wherein the set of rules comprises a normalization database or table.

5. The system according to claim 2, wherein, the normalized data associated with the digital documents is stored as meta data associated with that digital document.

6. The system according to claim 2, wherein said documentation computer communicates with a third-party computer to verify the authenticity of the digital documents.

7. The system according to claim 1, wherein the parameters defined by the healthcare provider computer define a format that the digital documents and normalized data is presented to the healthcare provider computer.

8. A method for processing on a documentation computer having a storage, medical personnel data of a medical personnel user transmitted from a medical personnel user computer, comprising:

receiving from the medical personnel user computer, medical personnel user personal information;

verifying the medical personnel user personal information by communication with a third-party computer to verify the authenticity of the medical personnel user personal information, and thereafter registering the medical personnel user as a validated registered medical personnel user of the system;

receiving from the medical personnel user digital documents, and data associated with the digital documents, on the documentation computer;

normalizing the data associated with the digital documents to create normalized data associated with the digital documents saving the digital documents and the normalized data in a storage of the documentation computer;

receiving instructions from said medical personnel user defining a set of rules governing access to the digital documents and data associated with the medical personnel user, including a defined time period;

saving the data associated with the medical personnel user and the set of rules governing access to the data associated with the user on the storage;

receiving healthcare provider data from a healthcare provider computer, verifying the healthcare provider data by communication with a third-party computer to verify the authenticity of the healthcare provider data, and thereafter registering the healthcare provider as a validated registered healthcare provider user of the system;

receiving data associated with the healthcare provider from the healthcare provider computer, the data associated with a healthcare provider comprising a set of rules governing a type and a format of digital documents to be received by the healthcare provider computer in connection with a medial contract;

receiving at the documentation computer, data associated with the medical personnel user and a medical contract that the medical personnel user has selected on a medical contract computer; and presenting at least some of the digital documents and the normalized data associated with the user to a healthcare provider computer associated with the medical contract for the defined time period and based on the set of rules governing access to the data associated with the medical personnel user and based on the healthcare provider set of rules.

9. The method according to claim 8, wherein the digital documents are selected from the group consisting of: certifications, school records, licenses, insurance documentation, continuing education certificates, fellowship program documentation, immunization records, physical exam records, malpractice records and combinations thereof.

10. The method according to claim 8, wherein the step of normalizing the data associated with the digital documents includes accessing a normalization database or table and determining equivalent nomenclature for at least one of the digital documents.

11. The method according to claim 10, wherein the normalized data associated with the digital documents is stored as meta data associated with the digital document.

12. The method according to claim 8, further comprising the steps of:

transmitting a verification request relating to the digital documents from the documentation computer to a third-party computer; and receiving a verification with the documentation computer that the digital documents are verified.

13. The system according to claim 1, wherein the documentation computer receives from the medical personnel user a set of rules governing access to the digital documents;

the documentation computer saves the set of rules governing access to the data associated with the medical personnel user on the storage; and the documentation computer presents at least some of the digital documents and the normalized data to the healthcare provider computer based on the set of rules received from the medical personnel user.

14. The method according to claim 8, further comprising the steps of:

the medical personnel user inputting setting up a set of rules governing access to the digital documents to the documentation computer;

saving the set of rules governing access to the data associated with the user on the storage;

the documentation computer presenting at least some of the digital documents and the normalized data to the healthcare provider computer based on the medical personnel user inputted set of rules governing access to the digital documents and the normalized data.

* * * * *